(12) United States Patent
Shaikh et al.

(10) Patent No.: US 9,663,434 B1
(45) Date of Patent: *May 30, 2017

(54) METHOD FOR HYDROFORMYLATING AN OLEFIN

(71) Applicant: KING FAHD UNIVERSITY OF PETROLEUM AND MINERALS, Dhahran (SA)

(72) Inventors: Mohammed Nasiruzzaman Shaikh, Dhahran (SA); Zain Hassan Yamani, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 0 days.

This patent is subject to a terminal disclaimer.

(21) Appl. No.: 15/281,855

(22) Filed: Sep. 30, 2016

Related U.S. Application Data

(63) Continuation of application No. 14/989,219, filed on Jan. 6, 2016, now Pat. No. 9,480,978.

(51) Int. Cl.
| | | |
|---|---|---|
| *C07C 45/50* | (2006.01) | |
| *B01J 31/00* | (2006.01) | |
| *C07F 15/02* | (2006.01) | |
| *B01J 31/02* | (2006.01) | |
| *B01J 35/00* | (2006.01) | |

(52) U.S. Cl.
CPC ......... *C07C 45/505* (2013.01); *B01J 31/0271* (2013.01); *B01J 35/0033* (2013.01); *C07F 15/025* (2013.01); *B01J 2231/321* (2013.01); *B01J 2531/004* (2013.01)

(58) Field of Classification Search
CPC ... C07C 45/505; B01J 31/2404; B01J 35/023; B01J 37/031
USPC .......................................................... 568/454
See application file for complete search history.

(56) References Cited

FOREIGN PATENT DOCUMENTS

WO    WO 2014/100630 A1    6/2014

OTHER PUBLICATIONS

Anja S. Goldmann, et al., "Biomimetic Mussel Adhesive Inspired Clickable Anchors Applied to the Functionalization of Fe3O4 Nanoparticles", URL: http://www.researchgate.net/publication/51122267_Biomimetic_mussel_adhesive_inspired_clickable_anchors_applied_to_the_functionalization_of_fe%283%29_o%284%29_nanoparticles, Total 1 Page, (2010).

Smolensky, Ed., et al., "Surface functionalization of magnetic iron oxide nanoparticles for MRI applications—effect of anchoring group and ligand exchange protocol", URL: http://www.ncbi.nlm.nih.gov/pubmed/21861279 Total 1 Page, (2011).

*Primary Examiner* — Sikarl Witherspoon
(74) *Attorney, Agent, or Firm* — Oblon, McClelland, Maier & Neustadt, L.L.P.

(57) ABSTRACT

A functionalized nanomaterial having an average particles size of less than 10 nm comprising an iron oxide nanoparticle core and a bis(diarylphosphinomethyl) dopamine based ligand layer anchored to the iron oxide nanoparticle core is disclosed. In addition, a catalyst composition for use in a variety of chemical transformations wherein the bisphosphine groups of the functionalized nanomaterial chelate a catalytic metal is disclosed. In addition, a method for producing the functionalized nanomaterial and a method for the hydroformylation of olefins to aldehydes employing the functionalized nanomaterial with high conversion percentage and high selectivity are disclosed.

7 Claims, 8 Drawing Sheets

METHOD FOR HYDROFORMYLATING AN OLEFIN

CROSS-REFERENCE TO RELATED APPLICATIONS

This application is a continuation application of Ser. No. 14/989,219, now allowed, filed on Jan. 6, 2016.

BACKGROUND OF THE INVENTION

Technical Field

The present disclosure relates to a functionalized nanomaterial comprising bis(diarylphosphinomethyl) dopamine based ligands anchored to iron oxide nanoparticles. Additionally, the present disclosure relates to methods for producing the functionalized nanomaterial and its application to chelate catalytic metals and catalyze chemical transformations involving those catalytic metals including the hydroformylation of olefins to aldehydes.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Aldehydes can be converted into a number of useful chemicals via condensation, hydrogenation, amination, etc. The catalyzed hydroformylation reaction is of significant commercial importance in the production of aldehydes from aliphatic as well as substituted aromatic olefins via syngas-mediated reactions. Approximately 11 million metric tons of oxo chemicals are produced and consumed per year worldwide with an annual growth rate of 4%. [S. K. Sharma and R. V. Jasra, *Catal. Today,* 2015, 247, 70.—incorporated herein by reference in its entirety]. Homogeneous catalytic processes have been extensively used for the alkene to aldehyde conversion [C. Claver, P. Kalack, L. A. Oro, M. T. Pinillos and Cristina Tejel, Journal of molecular Catalysts, 1987, 43, 1; A. Orejon, C. Claver, L. A. Oro, A. Elduque and M. T. Pinillos, Journal of Molecular Catalysis A: Chemical 1998, 136, 279; A. B. Rivas, J. J. Pérez-Torrente, A. J. Pardey, A. M. Masdeu-Bultó, Montserrat Diéguez and Luis A. Oro, Journal of Molecular Catalysis A: Chemical 2009, 300, 121; J. Norinder, C. Rodrigues, A. Börner, Journal of Molecular Catalysis A: Chemical 2014, 391, 139; M. Jouffroy, R. Gramage-Doria, D. Armspach, D. Semeril, W. Oberhauser, D. Matt, and L. Toupet, Angew. Chem. Int. Ed. 2014, 53, 3937; L. C. Matsinha, S. F. Mapolie, and G. S. Smith, Dalton Trans., 2015, 44, 1240; P. Dydio, R. J. Detz, B. D. Bruin, and J. N. H. Reek, J. Am. Chem. Soc. 2014, 136, 8418; T. T. Adint and C. R. Landis, J. Am. Chem. Soc. 2014, 136, 7943; L. Wu, I. Fleischer, R. Jackstell, I. Profir, R. Franke, and Matthias Beller, J. Am. Chem. Soc. 2013, 135, 14306; and Z. Nairoukh, J. Blum, Journal of Molecular Catalysis A: Chemical 2012, 358, 129—each incorporated herein by reference in its entirety]. However, the challenges in separation are paramount and the cost of separation is prohibitively high in terms of the need to use fairly expensive chemicals and fairly large amounts of precious metals.

In the past two decades, great efforts have been devoted toward developing alternatives to homogeneous catalysis to minimize the separation cost and maximize the product purity. Heterogeneous catalysis offers the ease of separation and reusability. Moreover, it minimizes the use of environmentally toxic solvents needed in large quantities for separation and purification [V. Polshettiwar and R. S. Varma, *Green Chem.,* 2010, 12, 743.—incorporated herein by reference in its entirety]. Most of the heterogeneous catalysts are supported on solids such as silica [V. Polshettiwar, B. Baruwati and R. S. Varma, Chem. Commun., 2009, 1837; K. Nozaki, Y. Itoi, F. Shibahara, E. Shirakawa, T. Ohta, H. Takaya and T. Hiyama, J. Am. Chem. Soc. 1998, 120, 4051; S. Ricken, P. W. Osinski, P. Eilbracht and R. Haag, J. Mol. Catal. A Chem. 2006, 257, 78; R. S. Varma, Pure Appl. Chem., 2013, 85, 1703; and A. R. McDonald, C. Muller, D. Vogt, G. P. M. van Klink and G. van Koten, Green Chem., 2008, 10, 424—each incorporated herein by reference in its entirety]. Silica is highly stable, robust and easy to functionalize; organic functional groups can be easily anchored via either covalent bonding or adsorption on the surface to provide catalytic centers [A. S. Kumar, M. A. Reddy, M. Knorn, O. Reiser, and B. Sreedhar, *Eur. J. Org. Chem.* 2013, 4674.—incorporated herein by reference in its entirety]. However, in most of the cases, a great number of catalytic sites are buried within the solid support, thereby resulting in a decrease in the overall reactivity. Leaching out of the catalyst by the cleavage of bonds between metal and ligand also hinders the ease of separation.

Due to their robustness and high surface area, nanoparticles have become favorable catalyst support systems [R. Abu-Reziq, H. Alper, D. Wang, and Michael L. Post, J. Am. Chem. Soc. 2013, 128, 5279; and J. P. K. Reynhardt, Y. Yang, A. Sayari and H. Alper, Adv. Synth. Catal. 2005, 347, 1379—each incorporated herein by reference in its entirety]; at nanoscale, the catalyst center may be more exposed to the reactant, thereby enhancing the activity. In this regard, superparamagnetic iron oxide nanoparticles (SPIONs) offer a promising research strategy to develop surface coated recyclable catalysts by anchoring homogeneous organic species (ligand or metal complexes) on the heterogeneous system, thus combining the advantages of both of the systems. In this context, a dendritic hydroformylation catalyst with excellent reactivity and selectivity attributes has recently been reported [R. Abu-Reziq, H. Alper, D. Wang, and Michael L. Post, *J. Am. Chem. Soc.* 2013, 128, 5279.—incorporated herein by reference in its entirety]. For these purposes, the chelating ligand, bis(diphenylphosphinomethyl) amine has proven itself for its interesting nature of coordination modes with different transition metals and its wide range of catalytic applications [T. T. Co and T.-J. Kim, *Chem. Commun.,* 2006, 3537—incorporated herein by reference in its entirety].

In view of the forgoing, one object of the present disclosure is to provide novel functionalized nanomaterials comprising bisphosphinated dopamine (bpd) based ligands anchored on nanostructured magnetic nanoparticles. A further aim of the present disclosure is to provide an economical and robust process for synthesizing and characterizing the produced functionalized nanomaterials. An additional aim of the present disclosure is to provide applications of the functionalized nanomaterials as recyclable and thermally stable catalysts once chelated with a catalytic metal in a wide variety of chemical transformations such as the conversion of olefins to aldehydes by hydroformylation using rhodium as the catalytic metal center.

BRIEF SUMMARY OF THE INVENTION

According to a first aspect, the present disclosure relates to a functionalized nanomaterial comprising i) an iron oxide nanoparticle core and ii) a bis(diarylphosphinomethyl) dopamine ligand, wherein the bis(diarylphosphinomethyl) dopamine ligand is anchored to a surface of the iron oxide nanoparticle core by phenolic hydroxide groups to form a bis(diarylphosphinomethyl) dopamine ligand layer and wherein the bisphosphine groups of the bis(diarylphosphinomethyl) dopamine ligand chelate a catalytic metal.

In one embodiment, the functionalized nanomaterial is in the form of particles having a spherical morphology and an average diameter of 1-20 nm.

In one embodiment, the functionalized nanomaterial has a phosphine content of 0.2-1.0 mmol of phosphine per gram of functionalized nanomaterial.

In one embodiment, the average thickness of the bis (diarylphosphinomethyl) dopamine ligand layer is less than 5 nm.

In one embodiment, the bis(diarylphosphinomethyl) dopamine ligand layer covers greater than 70% of the surface of the iron oxide nanoparticle core.

In one embodiment, the iron oxide nanoparticle core comprises magnetite, $Fe_3O_4$.

In one embodiment, the bis(diarylphosphinomethyl) dopamine ligand is bis(diphenylphosphinomethyl) dopamine.

In one embodiment, the functionalized nanomaterial loses less than 1% of its total weight after heating at a temperature of 200° C. and less than 10% of its total weight after heating at a temperature of 500° C.

According to a second aspect, the present disclosure relates to a process for producing the functionalized nanomaterial in any of its embodiments comprising i) reacting paraformaldehyde with a phosphine to produce a phosphinomethanol ii) reacting the phosphinomethanol with a dopamine salt to form the bis(diarylphosphinomethyl) dopamine ligand and iii) mixing the bis(diarylphosphinomethyl) dopamine ligand with the iron oxide nanoparticle core to form the functionalized nanomaterial.

In one embodiment, the iron oxide nanoparticle core is formed by precipitating an iron salt under alkaline conditions.

According to a third aspect, the present disclosure relates to a method for hydroformylating an olefin to a corresponding aldehyde comprising i) mixing the functionalized nanomaterial with the olefin ii) adding a rhodium salt as source of the catalytic metal and iii) hydroformylating the olefin in the presence of carbon monoxide or a carbon monoxide surrogate to form the corresponding aldehyde.

In one embodiment, the method further comprises recovering and reusing the functionalized nanomaterial in at least 2 reaction iterations.

In one embodiment, the rhodium salt comprises rhodium (III) chloride, $RhCl_3$ or 2,5-norbornadiene-rhodium (I) chloride dimer, $[Rh(NBD)Cl]_2$.

In one embodiment, the olefin is a styrene.

In one embodiment, a percent conversion from the olefin to the corresponding aldehyde is greater than 90%.

In one embodiment, the mixing involves no more than 50 mg of functionalized nanomaterial per 1.0 mmol of olefin.

In one embodiment, the corresponding aldehyde has a linear aldehyde form and a branched aldehyde form and the ratio of the linear aldehyde form to the branched aldehyde form is greater than or equal to 1.

According to a fourth aspect, the present disclosure relates to a catalyst composition comprising the functionalized nanomaterial and a catalytic metal, wherein the bisphosphine groups of the bis(diarylphosphinomethyl) dopamine ligand of the functionalized nanomaterial chelate the catalytic metal.

In one embodiment, the catalytic metal is at least one selected from the group consisting of nickel, platinum, palladium, rhodium, iron, gold, silver, ruthenium and iridium.

In one embodiment, the catalyst composition is employed in at least one chemical transformation selected from the group consisting of hydrogenations, palladium-catalyzed coupling reactions and selective oxidations.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
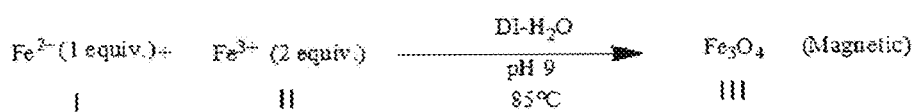
FIG. 1 is chemical reaction scheme for the synthesis of the iron oxide nanoparticle core wherein (I) is a source of $Fe^{2+}$ such as $FeCl_2$, (II) is a source of $Fe^{3+}$ such as $FeCl_3$, and (III) is the iron oxide nanoparticle core.

Referring now to the drawings, wherein, like reference numerals designate identical or corresponding parts throughout the several views.

According to a first aspect, the present disclosure relates to a functionalized nanomaterial including an iron oxide nanoparticle core. Iron oxides are chemical compounds composed of iron and oxygen. Iron oxides are widely used and typically colored yellow, orange, red, brown or black. There are sixteen known iron oxides and oxyhydroxides. The oxides include iron (II) oxide (wustite, FeO), iron (II,III) oxide (magnetite, $Fe_3O_4$), $Fe_4O_5$, $Fe_4O_3$, and iron (III) oxide including the alpha phase (hematite, $\alpha\text{-}Fe_2O_3$), beta phase ($\beta\text{-}Fe_2O_3$), gamma phase (maghemite, $\gamma\text{-}Fe_2O_3$) and epsilon phase ($\epsilon\text{-}Fe_2O_3$). The hydroxides include iron (II) hydroxide ($Fe(OH)_2$) and iron (III) hydroxide (bernalite, $Fe(OH)_3$). The oxide/hydroxides include goethite ($\alpha$-FeOOH), akaganeite ($\beta$-FeOOH), feroxyhyte ($\delta$-FeOOH), ferrihydrite ($Fe_5HO_8.4H_2O$ approx. or $5Fe_2O_3.H_2O$, better recast as $FeOOH.0.4H_2O$), high pressure FeOOH, Schertmannite (ideally $Fe_8O_8(OH)_6(SO).nH_2O$ or $Fe^{3+}_{16}O_{16}(OH,SO_4)_{12-13}.10\text{-}12H_2O$) and green rust ($Fe^{III}_xFe^{II}_y(OH)_{3x+2y-z}(A^-)_z$ where $A^-$ is $Cl^-$ or $0.5SO_4^{2-}$). In terms of the present disclosure, the iron oxide nanoparticle core may comprise any of the known iron oxides or oxyhydroxides above and mixtures thereof.

Iron (III) oxide or ferric oxide is the inorganic compound with formula $Fe_2O_3$. It is one of the three main oxides of iron, the other two being iron (II) oxide (FeO) which is rare, and iron (II,III) oxide ($Fe_3O_4$) which also occurs naturally as the mineral magnetite. $Fe_2O_3$ is ferromagnetic, dark red and readily attacked by acids. $Fe_2O_3$ can be obtained in various polymorphs. In the major polymorphs, $\alpha$ and $\gamma$, iron adopts an octahedral coordination geometry, each Fe center is bound to six oxygen ligands. $\alpha\text{-}Fe_2O_3$ has the rhombohedral corundum ($\alpha\text{-}Al_2O_3$) structure and is the most common form. It occurs naturally as the mineral hematite which is mined as the main ore of iron. $\gamma\text{-}Fe_2O_3$ has a cubic structure, is metastable and converted to the alpha phase at high temperatures. It is also ferromagnetic. Several other phases have been identified, including the $\beta$-phase, which is cubic body centered, metastable, and at temperatures above 500° C. converts to alpha phase, and the epsilon phase, which is rhombic, and shows properties intermediate between alpha and gamma phase. This phase is also metastable, transforming to the alpha phase between 500 and 750° C. Additionally, at high pressure an iron oxide can exist in an amorphous form. The iron oxide in the iron oxide nanoparticle core may be iron (III) oxide and may have an $\alpha$ polymorph, a $\beta$ polymorph, a $\gamma$ polymorph, a $\epsilon$ polymorph or mixtures thereof.

Iron (II, III) oxide or magnetite is another main oxide of iron with formula $Fe_3O_4$. It contains both $Fe^{2+}$ and $Fe^{3+}$ ions and is sometimes formulated as $FeO.Fe_2O_3$. It exhibits permanent magnetism and is ferrimagnetic, although sometimes described as ferromagnetic. Its particle size and shape can be varied by the method of production. $Fe_3O_4$ has a cubic inverse spinel structure which consists of a cubic close packed array of oxide ions where all of the $Fe^{2+}$ ions occupy half of the octahedral sites and the $Fe^{3+}$ are split evenly across the remaining octahedral sites and the tetrahedral sites. Both FeO and $\gamma\text{-}Fe_2O_3$ have a similar cubic close packed array of oxide ions and this accounts for the interchangability between the three compounds on oxidation and reduction as these reactions entail a relatively small change to the overall structure. $Fe_3O_4$ samples can be non-stoichiometric. In a preferred embodiment, the iron oxide nanoparticle core is substantially magnetite, $Fe_3O_4$.

Due to its four unpaired electrons in the 3d shell, an iron atom has a strong magnetic moment. $Fe^{2+}$ ions also have four unpaired electrons in the 3d shell and $Fe^{3+}$ ions have five unpaired electrons in the 3d shell. Thus, when crystals are formed from iron atoms or $Fe^{2+}$ and $Fe^{3+}$ ions they can be ferromagnetic, antiferromagnetic or ferrimagnetic states. The ferrimagnetism of $Fe_3O_4$ arises because the electron spins of the $Fe^{II}$ and $Fe^{III}$ ions in the octahedral sites are coupled and the spins of the $Fe^{III}$ ions in the tetrahedral sites are coupled but anti-parallel to the former. The net effect is that the magnetic contributions of both sets are not balanced and there is permanent magnetism.

In the paramagnetic state, the individual atomic magnetic moments are randomly oriented, and the substance has a zero net magnetic moment if there is no magnetic field. These materials have a relative magnetic permeability greater than one and are attracted to magnetic fields. The magnetic moment drops to zero when the applied field is removed. However, in a ferromagnetic material, all the atomic moments are aligned even without an external field. A ferrimagnetic material is similar to a ferromagnet but has two different types of atoms with opposing magnetic moments. The material has a magnetic moment because the opposing moments have different strengths. If they have the same magnitude, the crystal is antiferromagnetic and possesses no net magnetic moment. Superparamagnetism is a form of magnetism, which appears in small ferrimagnetic or ferromagnetic nanoparticles. In sufficiently small nanoparticles, magnetization can randomly flip direction under the influence of temperature. In a preferred embodiment, the iron oxide nanoparticle core is superparamagnetic, paramagnetic, ferromagnetic, antiferromagnetic and/or ferrimagnetic, more preferably the iron oxide in the iron oxide nanoparticle core possesses permanent magnetism and comprises magnetite ($Fe_3O_4$) and/or its oxidized form maghemite ($\gamma\text{-}Fe_2O_3$), most preferably the iron oxide in the iron oxide nanoparticle core possess permanent magnetism and is magnetite ($Fe_3O_4$).

The term "iron oxide nanoparticle core" as used herein refers to an iron oxide rich material (i.e. greater than 60%, preferably greater than 70%, preferably greater than 80%, more preferably greater than 90%, more preferably greater than greater than 95%) onto which a single or a plurality of bis(diarylphosphinomethyl) dopamine based ligands are anchored to form a functionalized nanomaterial. In a preferred embodiment the iron oxide nanoparticle core is a maghemite ($\gamma\text{-}Fe_2O_3$) rich material (i.e. greater than 40%, preferably greater than 50%, preferably greater than 60%, preferably greater than 70%, preferably greater than 80%, more preferably greater than 90%, more preferably greater than greater than 95% maghemite). In a most preferred embodiment the iron oxide nanoparticle core is a magnetite ($Fe_3O_4$) rich material (i.e. greater than 60%, preferably greater than 70%, preferably greater than 80%, more preferably greater than 90%, more preferably greater than greater than 95% magnetite).

In a most preferred embodiment, the iron oxide nanoparticle core of the functionalized nanomaterial is magnetite ($Fe_3O_4$).

In addition to iron oxide, it is envisaged that the present disclosure may be adapted to incorporate other metal oxide nanoparticles as a part of the functionalized nanomaterial. Exemplary metal oxides need only be generally of low cost and preferably (or optionally) magnetic. Examples of other metal oxides include, but are not limited to, oxides of aluminum, zinc, copper, nickel, magnesium, zirconium, titanium, vanadium, rhodium, rhenium, silicon, molybdenum, thorium, chromium, manganese, cerium, silver, lead, cadmium, calcium, antimony, tin, bismuth, cobalt, tungsten and alloys or mixtures thereof.

In addition to iron oxide and/or iron, various non-ferrous materials (i.e. metals and non-metals) may be present in the iron oxide nanoparticle core including, but not limited to, aluminum, cobalt, copper, lead, nickel, tin, titanium, zinc, bronze, gold, silver, platinum, palladium, metal oxides thereof, metal sulfides thereof, calcium oxide, magnesium oxide, magnesite, dolomite, aluminum oxide, manganese oxide, silica, sulfur, phosphorous and combinations thereof. The total weight percent of these non-ferrous materials relative to the total weight of the iron oxide nanoparticle core is preferably no more than 30%, preferably no more than 20%, preferably no more than 15%, preferably no more than 10%, preferably no more than 5%, preferably no more than 4%, preferably no more than 3%, preferably no more than 2%, preferably no more than 1%, preferably no more than 0.5%.

The functionalized nanomaterials of the present disclosure also include a bis(phosphinomethyl) and/or bis(diarylphosphinomethyl) dopamine based ligand anchored to the surface of the iron oxide nanoparticle core by phenolic hydroxide groups to form a bis(phosphinomethyl) and/or bis(diarylphosphinomethyl) dopamine based ligand layer, and wherein the bisphosphine groups of the bis(phosphinomethyl) and/or bis(diarylphosphinomethyl) dopamine based ligand chelate a catalytic metal or metal compound. As used herein, the terms "bis(phosphinomethyl) dopamine ligand" and "bis(phosphinomethyl) dopamine based ligand" and "bis(diarylphosphinomethyl) dopamine ligand and "bis (diarylphosphinomethyl) dopamine based ligand" are used interchangeably and may refer to all the dopamine ligands and dopamine derivative ligands described herein. The iron oxide nanoparticle core with a bis(phosphinomethyl) and/or bis(diarylphosphinomethyl) dopamine based ligand layer anchored to it is referred to herein as a "functionalized nanomaterial".

In a most preferred embodiment, the bis(phosphinomethyl) dopamine based ligand is bis(diarylphosphinomethyl dopamine based ligand, most preferably the bis(phosphinomethyl) dopamine based ligand is bis(diphenylphosphinomethyl) dopamine.

Chemically, a dopamine molecule (FIG. 2, compound VI shows the HCl salt) consists of a catechol structure (a benzene ring with two hydroxyl side groups) with one amine group attached. As such, dopamine is the simplest possible catecholamine, a family that also includes the neurotransmitters norepinephrine and epinephrine, additionally the presence of the benzene ring with an attached amine group makes it a phenethylamine. Phenethylamine is a primary amine, the amino group being attached to a benzene ring through a two-carbon or ethyl group. As used herein, the "bis(phosphinomethyl) dopamine based ligand" and/or "bis (diarylphosphinomethyl) dopamine based ligand" refers to a phenethylamine derivative with at least one, preferably two or more phenolic hydroxide groups, and a tertiary amine with one sidechain of the formula —CH$_2$PR$_1$R$_2$ and another sidechain of the formula —CH$_2$PR$_3$R$_4$, preferably one sidechain of the formula —CH$_2$PAr$_1$Ar$_2$ and another sidechain of the formula —CH$_2$PAr$_3$Ar$_4$, wherein Ar denotes an optionally substituted aryl group. The generic structure is shown (structure I):

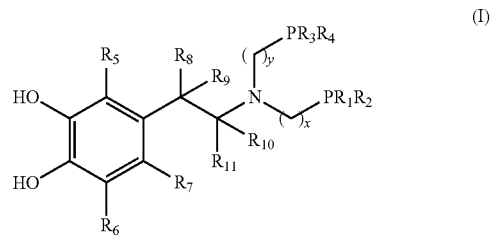

As used herein, the term "aryl" unless otherwise specified refers to functional groups or substituents derived from an aromatic ring including, but not limited to, phenyl, biphenyl, naphthyl, thienyl, and indolyl and other heteroaryls. As used herein, the term optionally includes both substituted and unsubstituted moieties. Exemplary moieties with which the aryl group can be substituted may be selected from the group including, but not limited to hydroxyl, halogen, amino, alkylamino, arylamino, alkoxy, aryloxy, nitro, cyano, sulfonic acid, sulfate, phosphonic acid, phosphate, or phosphonate or mixtures thereof. The substituted moiety may be either protected or unprotected as necessary, and as known to those skilled in the art.

In a preferred embodiment, the benzene group of the bis(diarylphosphinomethyl) dopamine based ligand comprises 1-5 phenolic hydroxide groups, preferably 2-4, preferably 2-3 or 2 as depicted in structure I. The phenolic hydroxide groups may be located ortho, para, or meta to the ethyl amine and mixtures thereof, preferably meta and/or para. In addition to the phenolic hydroxide(s), the benzene ring may be modified at any positions with groups for $R_5$-$R_7$ that may include, but are not limited to halogen groups, $C_1$-$C_{10}$ alkyl chains, alkoxyl groups, nitro groups, amino groups, mixtures thereof and the like.

In a preferred embodiment, the $R_1$, $R_2$, $R_3$ and $R_4$ groups of the bis(phosphinomethyl) dopamine based ligand are all the same, preferably aryl, most preferably phenyl. In another embodiment three of the four may be the same, in another embodiment two of the four may be the same, preferably on the same side chain, and in another embodiment $R_1$, $R_2$, $R_3$ and $R_4$ may all be different. The $R_1$-$R_4$ groups may include, but are not limited to, straight $C_1$-$C_{10}$ alkyl chains (i.e. methyl, ethyl), branched $C_1$-$C_{10}$ alkyl chains (i.e isopropyl), unsubstituted phenyl groups (Ph), and substituted phenyl groups.

In another embodiment, the tertiary amine of the bis (phosphinomethyl) dopamine based ligand may have sidechains of the formula $(CH_2)_xPR_1R_2$ and $(CH_2)_yPR_3R_4$ and/or $(CH_2)_xPAr_1Ar_2$ and $(CH_2)_yPAr_3Ar_4$ where x and y may be the same or x and y may be different and x and y may have values in the range of 1-10, preferably 1-8, preferably 1-6, preferably 1-5, preferably 1-4, preferably 1-3, preferably 1-2 or 1. In another embodiment, the tertiary amine is attached to the benzene ring through a 1-10 carbon group rather than a generic 2 carbon or ethyl group, preferably 2-8, preferably 2-6, preferably a 2-4 carbon group which can be modified with $R_8$-$R_{11}$ groups including, but not limited to halogen groups, alcohol groups, ester groups, amine groups, carbonyl groups and amide groups along the carbon chain.

In another embodiment, the benzene ring may be any appropriately sized aromatic hydrocarbon or heterocycle ring system.

In a most preferred embodiment, the bis(phosphinomethyl) dopamine based ligand is a bis(diarylphosphinomethyl) dopamine based ligand. In a most preferred embodiment, the bis(diarylphosphinomethyl) dopamine based ligand is bis(diphenylphosphinomethyl) dopamine. The phenethylamine has two phenolic hydroxide groups located meta and para to the ethyl amine and $R_1=R_2=R_3=R_4=Ph$ and $R_5$-$R_{11}=H$. In an alternative embodiment, the ligand layer comprises bis(phosphinomethyl) norepinephrine based ligands.

The molecular structure of the bis(phosphinomethyl) and/or bis(diarylphosphinomethyl) dopamine based ligand features at least one phenolic hydroxide, preferably two, in a single molecule. In one embodiment, these phenolic hydroxide groups are an anchor group that binds the iron oxide nanoparticle core. In one embodiment, the phenolic hydroxide groups covalently bind the $Fe^{2+}$ and/or $Fe^{3+}$ ions comprising the iron oxide nanoparticle core, preferably two phenolic hydroxide groups covalently bind. In one embodiment, it is envisaged that all phenolic hydroxide groups of the bis(diarylphosphinomethyl) dopamine based ligand bind the iron oxide nanoparticle core. In another embodiment one or more of the phenolic hydroxide groups of the bis(diarylphosphinomethyl) dopamine based ligand may not bind the iron oxide nanoparticle core and may be located on the outer surface or be covalently modified.

In a preferred embodiment, the bisphosphine groups of the bis(diarylphosphinomethyl) dopamine based ligand of the functionalized nanomaterial are oriented to chelate a catalytic metal. Chelation describes a particular way that ions and molecules bind metal ions. Chelation involves the formation or presence of two or more separate coordinate bonds between a polydentate (multiple bonded) ligand and a single central atom. In a preferred embodiment, the catalytic metal is at least one selected from the group consisting of nickel, platinum, palladium, rhodium, iron, gold, silver, ruthenium and iridium.

Nanoparticles are particles between 1 and 100 nm ($10^2$ and $10^7$ atoms) in size. A particle is defined as a small object that behaves as a whole unit with respect to its transport and properties. The exceptionally high surface area to volume ratio of nanoparticles may cause the nanoparticles to exhibit significantly different or even novel properties from those observed in individual atoms/molecules, fine particles and/or bulk materials. Nanoparticles can be classified according to their dimensions. Three-dimensional nanoparticles have all dimensions of less than 100 nm, and generally encompass isodimensional nanoparticles. Examples of three dimensional nanoparticles include, but are not limited to, nanoparticles, nanospheres, nanogranules and nanobeads. Two-dimensional nanoparticles have two dimensions of less than 100 nm, generally including diameter. Examples of two-dimensional nanoparticles include, but are not limited to, nanotubes, nanofibers and nanowhiskers. One-dimensional nanoparticles have one dimension of less than 100 nm, generally thickness. Examples of one-dimensional nanoparticles include, but are not limited to, nanosheets, nanoplatelets, nanolaminas and nanoshells. The iron oxide nanoparticle core and the functionalized nanomaterial of the present disclosure are preferably three-dimensional nanoparticles, but may also be one-dimensional, two-dimensional, three-dimensional or mixtures thereof.

In the present disclosure, the iron oxide nanoparticle core is covered with a thin coating or bis(diarylphosphinomethyl) dopamine based ligand layer which may be continuous or discontinuous. Therefore, the general shape and size of the iron oxide nanoparticle core may dictate the shape and size of the functionalized nanomaterial described herein. Nanoparticles are named for the real-world shapes that they appear to represent. These morphologies sometimes arise spontaneously as an effect of the synthesis or from the innate crystallographic growth patterns of the materials themselves. Some of these morphologies may serve a purpose, such as bridging an electrical junction.

In a preferred embodiment, the iron oxide nanoparticle cores and functionalized nanomaterials of the present disclosure are in the form of a nanoparticle, which is spherical or substantially spherical (e.g. oval, oblong, etc.) in shape. Alternatively, it is envisaged that the iron oxide nanoparticles may have a more polygonal shape and may be generally cubic or rectangular. However, the iron oxide nanoparticles disclosed herein may have various shapes other than spheres and may be of any shape that provides desired synthetic activity and/or desired properties in the resulting functionalized nanomaterial. In a preferred embodiment, the iron oxide nanoparticle cores and the functionalized nanomaterial have a spherical morphology.

In one embodiment, the iron oxide nanoparticle core and the functionalized nanomaterial of the present disclosure are envisaged to be synthesized and formed into a variety of morphologies and forms including, but not limited to, nanoparticles, nanosheets, nanoplatelets, nanocrystals, nanospheres, nanorectangles, nanotriangles, nanopentagons, nanohexagons, nanoprisms, nanodisks, nanocubes, nanowires, nanofibers, nanoribbons, nanorods, nanotubes, nanocylinders, nanogranules, nanowhiskers, nanoflakes, nanofoils, nanopowders, nanoboxes, nanostars, tetrapods, nanobelts, nanaourchins, nanofloweres, etc. and mixtures thereof.

In one embodiment, the iron oxide nanoparticle core and the functionalized nanomaterial have uniform shape. Alternatively, the shape may be non-uniform. As used herein, the term "uniform" refers to an average consistent shape that differs by no more than 10%, by no more than 5%, by no more than 4%, by no more than 3%, by no more than 2%, by no more than 1% of the distribution of iron oxide nanoparticles having a different shape. As used herein, the term "non-uniform" refers to an average consistent shape that differs by more than 10% of the distribution of iron oxide nanoparticles having a different shape. In one embodiment, the shape is uniform and at least 90% of the functionalized nanomaterial are spherical or substantially circular, and less than 10% are polygonal or substantially square. In another embodiment, the shape is non-uniform and less than 90% of the functionalized nanomaterial are spherical or substantially circular, and greater than 10% are polygonal or substantially square.

Nanoparticle characterization is necessary to establish understanding and control of nanoparticle synthesis, assembly and application. In one embodiment, the nanoparticles and functionalized nanomaterial are characterized by at least one technique selected from the group consisting of electron microscopy (TEM, SEM, FESEM), powder X-ray diffraction (XRD), thermogravimetric analysis (TGA) and Fourier transform infrared spectroscopy (FT-IR). In another embodiment, it is envisioned that characterization is done using a variety of other techniques. Exemplary techniques include, but are not limited to, ultraviolet-visible spectroscopy (UV-Vis), atomic force microscopy (AFM), dynamic light scattering (DLS), X-ray photoelectron spectroscopy (XPS), X-ray fluorescence (XRF), energy-dispersive X-ray spectroscopy (EDX), matrix-assisted laser desorption/ionization time-of-flight mass spectrometry (MALDI-TOF), Raman spectroscopy, Rutherford backscattering spectrometry (RBS), dual polarization interferometry, and nuclear magnetic resonance (NMR) or mixtures thereof.

The size of the iron oxide nanoparticle core may also dictate the size of the functionalized nanomaterial described herein. For spherical or substantially spherical iron oxide nanoparticles, average particle size refers to the average longest linear diameter of the iron oxide nanoparticles. For non-spherical iron oxide nanoparticles, such as cubes, squares and/or rectangles the average particle size may refer to the longest linear dimension and any of the length, width or height. In one embodiment, the functionalized nanomaterial of the present disclosure are monodispersed with an average particle size of 1-20 nm, preferably 2-15 nm, preferably 3-10 nm, preferably 4-8 nm, or most preferably 5-7 nm. In one embodiment, the functionalized nanomaterial of the present disclosure are monodispersed with an average particle size of greater than 20 nm, preferably 20-1000 nm, preferably 20-500 nm, preferably 20-250 nm, preferably 20-200 nm, preferably 20-150 nm, preferably 20-100 nm, preferably 20-75 nm, preferably 20-50 nm, preferably 20-40 nm, preferably 20-30 nm. The size may vary from these ranges and still provide acceptable functionalized nanomaterial.

In a preferred embodiment, the iron oxide nanoparticle core and functionalized nanomaterial of the present disclosure are monodisperse, having a coefficient of variation or relative standard deviation, expressed as a percentage and defined as the ratio of the particle size standard deviation ($\sigma$) to the particle size mean ($\mu$) multiplied by 100 of less than 25%, preferably less than 20%, preferably less than 15%, preferably, less than 12%, preferably less than 10%, preferably less than 8%, preferably less than 6%, preferably less than 5%, preferably less than 4%, preferably less than 3%, preferably less than 2%. In a preferred embodiment, the iron oxide nanoparticle core and functionalized nanomaterial of the present disclosure are monodisperse having a particle size distribution ranging from 80% of the average particle size to 120% of the average particle size, preferably 90-110%, preferably 95-105% of the average particle size.

In one embodiment, the bis(diarylphosphinomethyl) dopamine based ligand layer may "substantially cover" the surface of the iron oxide nanoparticle core, whereby the percent surface area coverage of the surface being covered is at least 70%, at least 75%, at least 85%, at least 90%, at least 95%, at least 96%, at least 97%, at least 98%, at least 99%. In another embodiment, the bis(diarylphosphinomethyl) dopamine based ligand layer may "incompletely cover", or only cover portions of the surface of the iron oxide nanoparticle core, whereby the percent surface area coverage of the surface being covered is less than 70%, less than 65%, less than 60%, less than 55%, less than 50%, less than 45%, less than 40%, less than 35%, less than 30%, less than 25%, less than 20%, less than 15%, or 10%.

The bis(diarylphosphinomethyl) dopamine based ligand layer may refer to one material (i.e. bis(methyldiphenylphosphino) dopamine and/or derivatives thereof) that covers the surface of the iron oxide nanoparticle core being functionalized, or alternatively the bis(diarylphosphinomethyl) dopamine based ligand layer may refer to a mixture of interspersed individual materials including bis(methyldiphenylphosphino) dopamine and one or more additional bis(phosphinomethyl) and/or bis(diarylphosphinomethyl) dopamine based ligands or other ligands or sequential applications of individual materials including bis(methyldiphenylphosphino) dopamine and one or more additional bis(phosphinomethyl) and/or bis(diarylphosphinomethyl) dopamine based ligands or other ligands. With sequential applications of individual materials, it may be possible to form distinct layers and these distinct layers may have a defined interface. The bis(phosphinomethyl) dopamine based ligand layer may also refer to a single application of a material or a plurality of applications of the same material and may comprise a monolayer, a bilayer, a trilayer and/or a multilayer.

In a preferred embodiment, the bis(diarylphosphinomethyl) dopamine based ligand layer substantially covers the iron oxide nanoparticle core, where the bis(diarylphosphinomethyl) dopamine based ligand covers greater than 70%, preferably greater than 75%, preferably greater than 80%, preferably greater than 85%, preferably greater than 90%, preferably greater than 95% of the surface of the iron oxide nanoparticle core. Alternatively, the bis(diarylphosphinomethyl) dopamine based ligand layer may only cover a portion of the surface of iron oxide nanoparticle core (i.e. incompletely cover), where the bis(diarylphosphinomethyl) dopamine based ligand layer covers less than 70%, less than 65%, less than 600%, less than 55%, less than 50%, less than 40%, less than 30%, less than 25%, less than 20%, less than 15%, less than 10% of the surface of the iron oxide nanoparticle core and the bis(diarylphosphinomethyl) dopamine based ligand layer may still provide sufficient functionalized nanomaterial for chelation of a catalytic metal.

In a preferred embodiment, the functionalized nanomaterial of the present disclosure has 0.2-1.0 mmol of phosphine per gram of functionalized nanomaterial, preferably 0.25-0.9 mmol per gram, preferably 0.3-0.8 mmol per gram, preferably 0.35-0.7 mmol per gram, preferably 0.4-0.6 mmol per gram, or 0.5 mmol of phosphine per gram of functionalized nanomaterial. It is envisaged that functionalized nanomaterials having phosphine loadings outside of these ranges may also function as intended.

In one embodiment, the functionalized nanomaterial of the present disclosure has a weight percentage of the bis(diarylphosphinomethyl) dopamine ligand layer ranging from 0.05-5.0%, preferably 0.1-2.5%, preferably 0.2-2.0%, preferably 0.25-1.5%, preferably 0.25-1.0% based on the total weight of bis(diarylphosphinomethyl) dopamine ligands bonded to the iron oxide nanoparticle core relative to the total weight of the functionalized nanomaterial. These ranges describe the bis(diarylphosphinomethyl) dopamine ligand when not bound to a catalytic metal, and it is envisaged that these ranges may change upon chelation to a catalytic metal, depending on the amount and type of catalytic metal.

In one embodiment, the average thickness of the bis(diarylphosphinomethyl) dopamine based ligand layer is less than 5 nm, preferably less than 4 nm, preferably less than 3.5 nm, preferably less than 3 nm, preferably less than 2.5 nm, preferably less than 2 nm, preferably less than 1.5 nm, preferably less than 1 nm. In a preferred embodiment, the bis(diarylphosphinomethyl) dopamine based ligand layer is of uniform thickness. Alternatively, the bis(diarylphosphinomethyl) dopamine based ligand layer may be of non-uniform thickness. The term "uniform thickness" refers to an average layer thickness that differs by no more than 5%, by no more than 4%, by no more than 3%, by no more than 2%, by no more than 1% at any given location on the surface of the iron oxide nanoparticle core. The term "non-uniform thickness" refers to an average layer thickness that differs by more than 5% at any given location on the surface of the iron oxide nanoparticle core.

The thermal stability as well as the strong attachment of the bis(diarylphosphinomethyl) dopamine based ligand to the iron oxide nanoparticle core are important for its functionality. In a preferred embodiment, the functionalized nanomaterial of the present disclosure loses less than 1% of its total weight when heated to a temperature of 200° C. Additionally, this weight loss may be entirely due to the loss of water molecules and not signify any loss of bound bis(diarylphosphinomethyl) dopamine based ligand. In a preferred embodiment, the functionalized nanomaterial of the present disclosure loses no more than 10% of its total weight, preferably no more than 7%, preferably no more than 5%, preferably no more than 4%, preferably no more than 3%, preferably no more than 2% of its total weight after heating at temperatures up to 200-500° C. for one hour. This weight loss may be attributed to the elimination of bis (diarylphosphinomethyl) dopamine based ligands in one or several steps. In a preferred embodiment, the functionalized nanomaterial loses no more than 75%, preferably no more than 50%, preferably no more than 40%, preferably no more than 30%, preferably no more than 25%, preferably no more than 20%, preferably no more than 15%, preferably no more than 10%, preferably no more than 5% of its bis(diarylphosphinomethyl) dopamine based ligands from the surface at temperatures of up to 500° C.

According to a second aspect, the present disclosure relates to a process for producing the functionalized nanomaterial of the present disclosure in any of its embodiments. The preparation method of the iron oxide nanomaterial has a large effect on shape, size distribution, and surface chemistry of the particles. It also determines the distribution and types of structural defects or impurities in the particles. All of these factors can affect the behavior, especially magnetic behavior, of the iron oxide nanoparticles.

In a preferred embodiment the iron oxide nanoparticle core is synthesized by coprecipitation techniques, i.e. by precipitating an iron salt under alkaline conditions. This method can be further divided into two types. The preferred type comprises ageing stoichiometric mixtures of ferrous and ferric hydroxides in aqueous media yielding spherical magnetite particles homogeneous in size. In the preferred type, the following chemical reaction occurs (formula I):

$$2Fe^{3+} + Fe^{2+} + 8OH^- \rightarrow Fe_3O_4 + 4H_2O \qquad (I):$$

The size and shape of the nanoparticles can be controlled by adjusting pH, ionic strength, temperature, nature of the salts (i.e. perchlorates, chlorides, sulfates and nitrates) and/or the Fe (II)/Fe (III) concentration ratio. Advantageous conditions for this reaction are a pH in the range of 8-14, preferably 8.25-12, preferably 8.5-10, preferably 8.75-9.75, most preferably 9. In a preferred embodiment, the pH is maintained by ammonium hydroxide but a variety of bases are envisaged, including hydroxide, carbonates and bicarbonates of alkali metals or alkaline earth metals. Advantageous conditions for this reaction are a ratio of 2:1 for $Fe^{3+}$ to $Fe^{2+}$. Advantageous conditions for this reaction are a non-oxidizing environment. Being highly susceptible to oxidation, magnetite ($Fe_3O_4$) is transformed to maghemite ($\gamma$-$Fe_2O_3$) in the presence of oxygen but the following chemical reaction (formula 2):

$$2Fe_3O_4 + O_2 \rightarrow 2\gamma Fe_2O_3 \qquad (II):$$

In another embodiment, the iron oxide nanoparticle core may be envisaged to be synthesized by the other type of coprecipitation technique. In this method, ferrous hydroxide suspensions are partially oxidized with different oxidizing agents. For example, spherical magnetite particles of narrow size distribution can be obtained from a Fe(II) salt, a base and a mild oxidant (i.e. nitrate ions).

In a preferred embodiment, the source of iron (III) is iron (III) chloride ($FeCl_3$). In another embodiment, it is envisaged that the present disclosure may be adapted to incorporate other sources of iron (III) in addition to iron (III) chloride including, but not limited to, iron (III) acetylacetonate, iron (III) nitrate, iron (III) tartrate, iron (III) sulfate, iron (III) trifluoromethanesulfonate, iron (III) bromide, iron (III) perchlorate, iron (III) phosphate, iron (III) oxalate, iron (III) fluoride, iron (III) p-toluenesulfonate and hydrates and/or mixtures thereof.

In a preferred embodiment, the source of iron (II) is iron (II) chloride ($FeCl_2$). In another embodiment, it is envisaged that the present disclosure may be adapted to incorporate other source of iron (II) in addition to iron (II) chloride including, but not limited to, iron (II) iodide, iron (II) sulfate, iron (II) acetate, iron (II) acetylacetonate, iron (II) oxalate, iron (II) bromide, iron (II) lactate, iron (II) molybdate, iron (II) perchlorate, iron (II) gluconate, iron (II) tetrafluoroborate, iron (II) fluoride, iron (II) fumarate, iron (II) trifluoromethanesulfonate, iron (II) ethylenediammonium sulfate and hydrates and/or mixtures thereof.

In another embodiment, the iron oxide nanoparticle core may be envisaged to be synthesized by microemulsion techniques. A microemulsion is a stable isotropic dispersion of 2 immiscible liquids consisting of nanosized domains of one or both liquids in the other stabilized by an interfacial film of surface-active molecules. Microemulsions may be categorized further as oil-in-water (o/w) or water-in-oil (w/o), depending on the dispersed and continuous phases. Water-in-oil is more popular for synthesizing many kinds of nanoparticles. The water and oil are mixed with an amphiphilic surfactant. The surfactant lowers the surface tension between water and oil, making the solution transparent. The water nanodroplets act as nanoreactors for synthesizing nanoparticles. The shape of the water pool is spherical. The size of the nanoparticles will depend on the size of the water pool to a great extent; thus, the size of the spherical nanoparticles can be tailored and tuned by changing the size of the water pool.

In another embodiment, the iron oxide nanoparticle core may be envisaged to be synthesized by high temperature decomposition of organic precursor techniques. The decomposition of iron precursors in the presence of hot organic surfactants results in samples with good size control, narrow size distribution and good crystallinity; and the nanoparticles are easily dispersed. Viable iron precursors include, but are not limited to, $Fe(Cup)_3$, $Fe(CO)_5$, or $Fe(acac)_3$ in organic solvents with surfactant molecules. A combination of xylenes and sodium dodecylbenzensulfonate as a surfactant are used to create nanoreactors for which well dispersed iron (II) and iron (III) salts can react.

The process for forming the bis(diarylphosphinomethyl) dopamine based ligand involves preparing phosphinoalcohol, preferably phosphine methanol, preferably diaryl phosphine methanol by the reaction of paraformaldehyde and desired phosphine of the formula ($HPR_1R_2$ or $HPR_3R_4$ and/or $HPAr_1Ar_2$ or $HPAr_3Ar_4$). In a preferred embodiment, the reaction is performed in a dry non-polar solvent (i.e. toluene) and heated to 50-200° C., preferably 80-150° C., preferably 90-140° C., preferably 100-130° C., preferably 110-125° C. or 120° C. for 2-12 hours, preferably 2-10 hours, preferably 2-8 hours, preferably 2-6 hours or 4 hours. In one embodiment, what begins as a turbid solution should become clear as the reaction proceeds. In the third step, a dopamine based salt, preferably dopamine hydrochloride, is added in situ to the above reaction mixture without isolation of the phosphinoalcohol and the reaction is heated at 50-200° C., preferably 80-150° C., preferably 90-140° C., preferably 100-130° C., preferably 110-125° C. or 120° C. for 2-48 hours, preferably 8-36 hours, preferably 12-36 hours, preferably 20-30 hours or 24 hours to form the bis(diarylphosphinomethyl) dopamine based ligand as a precipitated sticky solid that after drying under vacuum is obtained as a cream colored solid in a yield of over 50% from the phosphine, preferably over 75%, preferably over 80%, preferably over 85%, preferably over 90%, preferably over 95%.

The functionalized nanomaterial is formed by mixing a solution or suspension of the prepared iron oxide nanoparticle cores with a solution or suspension of the prepared bis(diarylphosphinomethyl) dopamine based ligand. The reaction is carried out by sonication for up to 12 hours, preferably up to 10 hours, preferably up to 8 hours, preferably up to 6 hours, preferably up to 4 hours, preferably up to 2 hours. The functionalized nanomaterial may be obtained as a light black colored powder that is collected with the aid of a strong magnet after washing repeatedly. In a preferred embodiment, the bis(diarylphosphinomethyl) dopamine based ligand is in an anhydrous polar protic solvent (i.e. short chain alcohols such as methanol, ethanol, n-propanol, isopropanol, n-butanol) and the iron oxide nanoparticles are in an anhydrous non-polar solvent (i.e. chloroform).

According to a third aspect, the present disclosure relates to a method for the hydroformylation of an olefin to a corresponding aldehyde utilizing the functionalized nanomaterial of the present disclosure in any of their embodiments. The method includes mixing the functionalized nanomaterial of the present disclosure in any of their embodiments with the olefin, adding a rhodium salt as a source of the catalytic metal and then hydroformylating the olefin in the presence of carbon monoxide or a carbon monoxide surrogate.

Hydroformylation, also known as oxo synthesis or oxo process is an important industrial process for the production of aldehydes from alkenes. This chemical reaction entails the addition of a formyl group (CHO) and a hydrogen atom to a carbon-carbon double bond. It is important because the resulting aldehydes are easily converted into many secondary products. For example, the resulting aldehydes are hydrogenated to alcohols that are converted to plasticizers or detergents. Hydroformylation is also used in specialty chemicals, relevant to the organic synthesis of fragrances and natural products. The process typically entails treatment of an alkene with high pressures (between 10-100 atmospheres) of carbon monoxide and hydrogen at temperatures between 40 and 200° C. Transition metal catalysts are required.

The overall mechanism resembles that for homogeneous hydrogenation with additional steps. The reaction begins with the generation of a coordinatively unsaturated metal hydrido carbonyl complex such as $HCo(CO)_3$ or $HRh(CO)(PPh_3)_3$. Such species bind alkenes, and the resulting complex undergoes a migratory insertion reaction to form an alkyl complex. After the alky formation a second migratory insertion converts the alkyl into an acetyl ligand, this is when the alkyl carbon forms a bond with the carbon of a carbonyl ligand. The vacant site on the metal is filled by two hydrogens, from the oxidative insertion of a hydrogen molecule. One of these hydrides then takes part in a reductive elimination to form the molecule of the aldehyde and the complex.

A key consideration of hydroformylation is the "normal" (linear) versus "iso" (branched) selectivity. For examples, the hydroformylation of propylene can afford two isomeric products, butyraldehyde or isobutyraldehyde. These isomers result from differing ways of inserting the alkene into the metal-hydrogen bond. Although, both products are equally desirable, significant effort has been dedicated to a catalyst that favors the normal or linear isomer. One controlling factor is steric effects. When the hydrogen is transferred to the carbon bearing the most hydrogen atoms (Markovnikov addition) the resulting alkyl group has a larger steric bulk close to the ligands of the metal. If the ligands on the metal are bulky (i.e. tributyl phosphine or diphenyl phosphine) then the steric effect is greater and the mixed carbonyl-phospine complexes offer a greater selectivity toward the straight chain linear products. Another controlling factor is electronic effects. The more electron-rich the hydride complex is the less proton-like the hydride is. Thus, as a result, the electronic effects that favor the Makovnikov addition to an alkene are less able to direct the hydride to the carbon atom bearing the most hydrogens already. Thus, as a result, as the metal center becomes more electron-rich, the catalyst becomes more selective for the straight chain linear compounds. In one embodiment, the corresponding aldehyde of the present disclosure has a linear ("normal") aldehyde form and a branched ("iso") aldehyde form and the ratio of the linear aldehyde form to branched aldehyde form is greater than or equal to 1, preferably greater than 1.05, preferably greater than 1.10, preferably greater than 1.15, preferably greater than 1.20, preferably greater than 1.3, preferably greater than 1.4, preferably greater than 1.5, preferably greater than 1.75, preferably greater than 2. In another embodiment, it is envisaged that the current method may be adapted to have a ratio of the linear aldehyde form to branched aldehyde form of less than 1, preferably less than 0.95, preferably less than 0.9, preferably less than 0.85, preferably less than 0.8, preferably less than 0.75, preferably less than 0.5, preferably less than 0.25.

In another embodiment, the hydroformylation of prochiral alkenes creates new stereocenters. Using chiral bis(phosphinomethyl) and/or bis(diarylphosphinomethyl) dopamine based ligands having chiral phosphine ligands, chiral dopamine based structures (e.g. norepinephrine) or both, the hydroformylation can be tailored to favor one enantiomer of the newly generated stereogenic center.

In a preferred embodiment, the percent conversion from the olefin to the corresponding aldehyde is greater than 90%, preferably greater than 91%, preferably greater than 92%, preferably greater than 93%, preferably greater than 94%, preferably greater than 95%, preferably greater than 96%, preferably greater than 97%, preferably greater than 98%, preferably greater than 99%, preferably greater than 99.5%, preferably greater than 99.9%. The percent conversion may vary from this range and still provide acceptable functionalized nanomaterial having increased selectivity for the linear aldehyde product versus the branched aldehyde product.

In one embodiment, the method for the hydroformylation of an olefin to a corresponding aldehyde utilizing the functionalized nanomaterial of the present disclosure in any of its embodiments further comprises recovering and reusing the functionalized nanomaterial in at least 2 reaction iterations, preferably at least 3, preferably at least 4, preferably at least 5, preferably at least 6, preferably at least 8, preferably at least 10, preferably at least 15, preferably at least 20 reaction iterations. The functionalized nanomaterial can be recovered via magnetic extraction and washed several times with a solvent such as dichloromethane to remove all materials present after each round of catalysis and then be recycled with an appropriate amount of rhodium. In a preferred embodiment, there is less than a 10% loss in percent conversion from the olefin to the corresponding aldehyde between the first and second iteration, preferably less than 5%, preferably less than 4%, preferably less than 3%, preferably less than 2% loss in percent conversion. In another embodiment, there is less than a 20% loss in percent conversion from the olefin to the corresponding aldehyde between the first and third iteration, preferably less than 15%, preferably less than 10% in percent conversion. In another embodiment, there is less than a 35% loss in percent conversion from the olefin to the corresponding aldehyde between the first and fourth iteration, preferably less than 30%, preferably less than 25%, preferably less than 20% loss in percent conversion.

The performance of the hydroformylation can be controlled by adjusting conditions such as temperature, pressure, solvent and/or catalyst loading. In a preferred embodiment, the hydroformylation is carried out at temperatures below 150° C., preferably below 125° C., preferably below 100° C., preferably below 90° C., preferably below 75° C., preferably below 50° C., preferably below 30° C. or at room temperature. In a preferred embodiment, the carbon monoxide surrogate is syngas or synthesis gas, a mixture comprising primarily hydrogen, carbon monoxide and often some carbon dioxide. In a preferred embodiment, the hydroformylation is carried out under less than 300 psi of pressure in the presence of syngas, preferably less than 275 psi, preferably less than 250 psi, preferably less than 225 psi, preferably less than 200 psi, preferably less than 150 psi of pressure in the presence of syngas. In a preferred embodiment, the hydroformylation is carried out in anhydrous solvent, preferably a non-polar solvent or a polar aprotic solvent. Exemplary non-polar solvents include, but are not limited to toluene, pentane, cyclopentane, hexane, cyclohexane, benzene, toluene, 1,4-dioxane, chloroform, diethyl ether and dichloromethane. Exemplary polar aprotic solvents include, but are not limited to, tetrahydrofuran (THF), ethyl acetate, acetone, dimethylformamide (DMF), acetonitrile (MeCN), dimethyl sulfoxide (DMSO), nitromethane and propylene carbonate. In a preferred embodiment, the hydroformylation is carried out using no more than 50 mg of functionalized nanomaterial per 1.0 mmol of olefin, preferably no more than 45 mg, preferably no more than 40 mg, preferably no more than 35 mg, preferably no more than 30 mg, preferably no more than 25 mg, preferably no more than 20 mg of functionalized nanomaterial per 1.0 mmol of olefin. The conditions may vary from these ranges and still provide acceptable conditions for performing the hydroformylation utilizing the functionalized nanomaterial of the present disclosure.

The general nature of the olefin substrate is not viewed as particularly limiting to the hydroformylation described herein. In one embodiment, the olefin is a styrene. Styrene, also known as ethenylbenzene, vinylbenzene, and phenylethene, is an organic compound with the chemical formula $C_6H_5CHCH_2$. The derivative of benzene is a colorless oily liquid that evaporates easily. It is envisaged that the present disclosure may be adapted to incorporate other styrene derivatives and the benzyl ring of styrene may be modified with a group $R_1$-$R_5$ which may include, but are not limited to, an electron withdrawing group, an electron donating group, halogen groups, $C_1$-$C_{10}$ alkyl chains, alkoxyl groups and the like and mixtures thereof. Exemplary styrene derivatives include, but are not limited to, styrene, 4-methylstyrene, 4-vinylanisole, 2-vinylanisole, 3-vinylanisole, 4-chlorostyrene, 3-nitrostyrene, 4-trifluoromethyl styrene, 3-trifluoromethyl styrene, 2-trifluoromethyl styrene, 4-[N-(methylaminoethyl)aminomethyl] styrene and mixtures thereof.

In a preferred embodiment, the rhodium salt and source of rhodium catalytic metal is rhodium (III) chloride, $RhCl_3$ of 2,5-norbornadiene-rhodium (I) chloride dimer, $[Rh(NBD)Cl]_2$. In another embodiment, it is envisaged that the present disclosure may be adapted to incorporate other sources of rhodium including, but not limited to, rhodium (III) nitrate, rhodium (III) acetylacetonate, rhodium (III) sulfate, ammonium hexachlororhodate (III), rhodium (III) oxide and hydrates and/or mixtures thereof. In another embodiment, it is envisaged that the present disclosure may be adapted to incorporate other sources of rhodium including, but not limited to chloro (1,5-cyclooctadiene) rhodium (I) dimer, bicycle [2.2.1]hepta-2,5-diene rhodium (I) chloride dimer, (acetylacetonato) (norbornadiene) rhodium (I), hydroxyl(cyclooctadiene) rhodium (I) dimer, chloro bis(cyclooctene) rhodium (1) dimer, methoxy (cyclooctadiene) rhodium (I) dimer, hydroxy [—(S)-BINAP] rhodium (I) dimer and hydrates and/or mixtures thereof. Furthermore, it is envisioned that the hydroformylation described herein may be adapted to incorporate alternative catalytic metals to rhodium, such as cobalt.

According to a fourth aspect, the present disclosure relates to a catalyst composition comprising the functionalized nanomaterial of the present disclosure in any of their embodiments and a catalytic metal, wherein the functionalized nanomaterial chelates the catalytic metal. In a preferred embodiment, the catalytic metal is at least one selected from the group consisting of nickel, platinum, palladium, rhodium, iron, gold, silver, ruthenium and iridium. The catalyst composition is envisioned to possess a wide range of catalytic applications from its coordination mode with different metals.

Heterogeneous catalysts refer to catalysts where the phase of the catalyst differs from that of the reactants. Homogeneous catalysts refer to catalysts where the phase of the catalyst is the same as that of the reactants. In terms of the present disclosure, the catalyst composition may function as a heterogeneous catalyst, a homogeneous catalyst, or have components that function and have properties of both a heterogeneous catalyst and a homogeneous catalyst.

In a preferred embodiment, the catalyst composition is employed in at least one chemical transformation selected from the group including, but not limited to, hydrogenations, palladium-catalyzed coupling reactions and selective oxidations.

In one embodiment, the catalytic composition may comprise the functionalized nanomaterial chelating rhodium and be employed in a chemical transformation such as a hydrogenation. In one embodiment, the hydrogenation may be an asymmetric hydrogenation. Exemplary rhodium catalyzed hydrogenations include, but are not limited to, the hydrogenation of alkenes, the hydrogenation of alkynes, the hydrogenation of aromatic cyclic arenes, the hydrogenation of nitriles, and the hydrogenation of pyridines and N-heterocycles.

In one embodiment, the catalytic composition may comprise the functionalized nanomaterial chelating palladium and be employed in a chemical transformation such as palladium-catalyzed coupling reactions. Exemplary palladium catalyzed coupling reactions include, but are not limited to, Negishi couplings (between an organohalide and an organozinc compound), Heck reactions (between alkenes and aryl halides), Suzuki reactions (between aryl halides and boronic acids), Stille reactions (between organohalides and organotin compounds), Hiyama couplings (between organhalides and organosilicon compounds), Sonagashira couplings (between aryl halides and alkynes, with copper (I) iodide as a co-catalyst), the Buchwald-Hartwig amination of an aryl halide with an amine, the Kumada coupling of grignards and aryl or vinyl halides, and the Heck-Matsuda reaction of an arenediazonium salt and an alkene.

In one embodiment, the catalytic composition may comprise the functionalized nanomaterial chelating palladium and/or platinum and be employed in a chemical transformation such as the selective oxidation of alcohols and aldehydes or allylic alkylations. In one embodiment, the catalytic composition may comprise the functionalized nanomaterial chelating palladium or ruthenium and be employed in a chemical transformation such as Suzuki reactions, Suzuki-Miyuara couplings, Miyuara-Heck couplings, Mizoroiki-Heck couplings, Heck arylations and vinylations, Tsuji-Trost reactions (additions to π-allyls), olefin metathesis and/or aromatic carbon-heteroatom bond forming reactions.

The examples below are intended to further illustrate protocols for preparing and characterizing the functionalized nanomaterial of the present disclosure. Further, they are intended to illustrate assessing the properties of these nanomaterials. They are not intended to limit the scope of the claims.

Example 1

Chemicals

All reactions were carried out under argon atmosphere using standard Schlenk technique. Chemicals were all purchased from Sigma-Aldrich Company and were utilized directly as received without further purification unless otherwise noted. Deionized (DI) water was obtained from a water purification system and used wherever needed.

Example 2

Synthesis of Magnetic Nanoparticles (MNPs)

Magnetite ($Fe_3O_4$) nanoparticles in the range of 5-7 nm were synthesized (FIG. 1) according to the procedure reported in the literature [J. Hee Yang, B. Ramaraj and K. R. Yoon, Journal of Alloys and Compounds 2014, 583, 128—incorporated herein by reference in its entirety]. The magnetic nanoparticles were prepared by co-precipitation techniques with the reaction of a 1:2 molar mixture of Fe (II) and Fe (III) precursors. The medium of the reaction was made alkaline using concentrated ammonium hydroxide and the pH was kept constant at 9 for 4 hours. The black colored solid materials were collected using a strong magnet after repeated washing with water to remove unreacted iron precursors (FIG. 1).

Briefly, 2 grams of hydrated $FeCl_2$ (10 mmol) and 8.08 g of $FeCl_3$ (20 mmol) were dissolved in 200 mL of deionized water under argon at 90° C. with vigorous stirring. Concentrated $NH_4OH$ was slowly added until the solution attained a pH of 9, attended by precipitation. The mixture was allowed to stand for 4 h. The precipitate (black) was washed several times with deionized (DI) water and dried.

Example 3

Synthesis of Bis(Methyldiphenylphosphino) Dopamine (Bpd) Ligand

Figure 2:
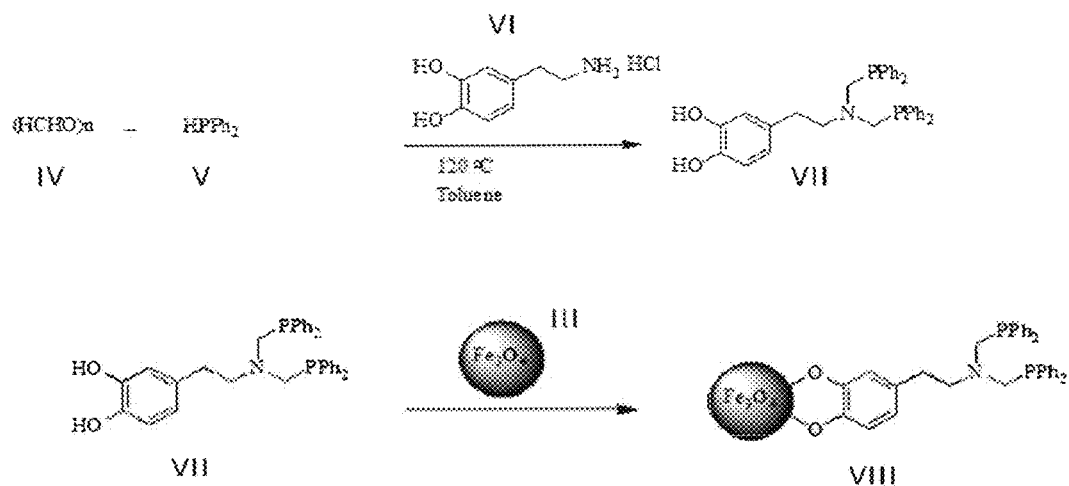
FIG. 2 is a chemical reaction scheme for the synthesis of the functionalized nanomaterial wherein (IV) is paraformaldehyde, (V) is a phosphine, (VI) is a dopamine based salt, (VII) is the bis(diarylphophinomethyl) dopamine based ligand, (III) is the iron oxide nanoparticle core, and (VIII) is the prepared functionalized nanomaterial.

Dopamine was functionalized by a double phosphinomethylation step on primary amine via reaction of dopamine hydrochloride and diphenylphosphinomethanol (FIG. 2). The first step of this reaction was to prepare phosphinoalcohol. Diphenylphosphine was allowed to react with paraformaldehyde in dry toluene under heating at 120° C. for 4 hours and the turbid solution became clear. The dopamine was phosphinylated using a straight forward reaction with quantitative yield [I. Angurell, C.-O. Turrin, R. Laurent, V. Maraval, P. Servin, O. Rossell, M. Seco, A.-M. Caminade and J.-P. Majora, *Journal of Organometallic Chemistry* 2007, 692, 1928; and P. Servin, R. Laurent, A. Romerosa, M. Peruzzini, J.-P. Majoral, and A.-M. Caminade, *Organometallics* 2008, 27, 2066—each incorporated herein by reference in its entirety]. In this reaction, equimolar amounts of dopamine hydrochloride were added in situ into the reaction system and it was heated to reflux at 120° C. for another 24 hours and subsequently precipitated as a sticky solid and after drying under vacuum was obtained as a cream color solid in 90% yield.

Briefly, 1.75 mL of diphenylphosphine (10 mmol) was added to the suspension of 2.9 g paraformaldehyde (9.5 mmol) in 10 mL anhydrous toluene under argon. The mixture was stirred for 4 h at 120° C. to obtain a clear solution. To this clear solution 0.76 g of dopamine hydrochloride (4 mmol) was added and the solution was refluxed for 24 h at 120° C. This resulted in a creamy suspension from which solid bis(methyldiphenylphosphino) dopamine ligand was obtained by filtration and subsequent washing, first with toluene and then with DI water. $^{31}P\{H\}$ NMR (200 MHz, in DMSO-$d_6$): δ −28.71 (s, $PPh_2$) ppm. $^1H$ NMR (500 MHz, DMSO-$d_6$): δ 2.49 (t, 2H, $NCH_2CH_2$), 3.69 (t, 2H, $NCH_2CH_2$), 4.14 (br d, 4H, $CH_2P$), 6.47 (br s, 2H, OH), 6.55 (2H, CH), 6.74 (br s, 1H, CH), 7.4 (br s, 12H, CH), 7.56 (br s, 8H, CH). FT-IR in KBr (in $cm^{-1}$); 3137, 2925, 2574, 1626, 1526, 1434, 1275.

Example 4

Synthesis of Functionalized Nanomaterial (MNPs@Bpd)

The surface of the magnetite nanoparticles (MNPs) were decorated through the hydroxyl group functionalized dopamine. The obtained bis(methyldiphenylphosphino) dopamine (bpd) ligand in anhydrous methanol was sonicated with the suspended solution of magnetite nanoparticles in chloroform for 6 hours and produced a light black colored powder after repeated washings with methanol. The magnetite nanoparticles were functionalized (FIG. 2) by modifying a reported procedure [C. Duanmu, L. Wu, J. Gu, X. Xu, L. Feng and Xu Gu, Catalysis Communications 2014, 48, 45—incorporated herein by reference in its entirety] as follows: 200 mg of magnetite nanoparticles were suspended in 10 mL of anhydrous $CHCl_3$ to which a solution containing 200 mg of bis(methyldiphenylphosphino) dopamine in anhydrous methanol was added under argon. The mixture was sonicated for 6 h. The functionalized nanomaterials were collected with the help of a strong magnet after washing repeatedly with methanol.

Example 5

Instrumentation

For solution nuclear magnetic resonance (NMR) analysis the $^1$H and $^{13}$C NMR signatures were collected on a Joel JNM-LA 500 Spectrometer and the respective chemical shifts (δ) were defined using tetramethylsilane (TMS) as an internal standard. For the $^{31}$P NMR, 85% $H_3PO_4$ was used as an internal reference. For the Fourier transform infrared (FT-IR) analysis the IR spectra of the functionalized magnetic nanoparticles were obtained from the Nicolet 720 in the range of 400 to 4000 cm$^{-1}$, using KBr. For the thermal gravimetric analysis (TGA) the thermal analysis was performed on the Mettler-Tolledo with model TGA1 STAR$^e$ System on around 10 mg of dry samples under argon atmosphere with the heating rate of 10° C./min and with the temperature range of 0-800° C./min.

For X-ray diffraction (XRD) analysis the diffraction data was collected on a Rigaku, model MiniFlex II diffractometer employing Cu-Kα radiation. The data was acquired over the 2θ range between 15 and 85. For inductively coupled plasma mass spectrometry (ICP-MS) analysis the phosphorous content in the sample was determined by the ICP-MS (Thermo Scientific, model XSERIES 2) by dissolving samples in concentrated $HNO_3$.

For scanning electron microscopy (SEM) and energy dispersive spectroscopy (EDS) analysis the surface morphology of the nanoparticles was discerned by a field emission scanning electron microscope (FESEM, LYRA 3 Dual Beam, Tescan) operated at 30 kV. SEM samples were prepared either from suspension or dry powder and coated with gold in an automatic gold coater for 90 s. The energy dispersive X-ray spectra (EDS) for the chemical and elemental analysis of the nanoparticles were also collected from the LYRA 3. For transmission electron microscopy (TEM) analysis the transmission electron imaging was done on a TEM (Joel, J E M 2011) operated at 200 kV with a 4 k×4 k CCD camera (Ultra Scan 400SP, Gatan). The TEM samples were prepared by dropping on a copper grid from an ethanolic suspension and drying at room temperature.

Example 6

Characterization of the Magnetic Nanoparticles (MNPs), Phosphinylated Ligand (Bpd) and Prepared Functionalized Nanomaterial (MNPs@Bpd)

Figure 3A:
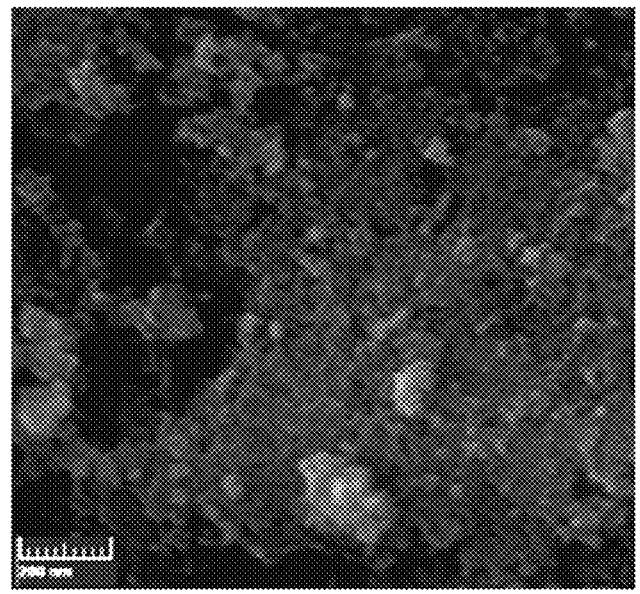
FIG. 3A is a scanning electron microscopy (SEM) image of the prepared functionalized nanomaterial.
Figure 3B:
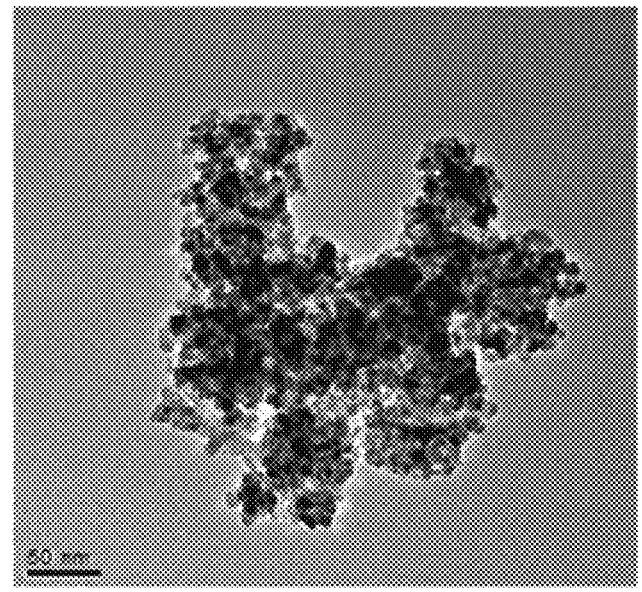
FIG. 3B is a transmission electron microscopy (TEM) image of the prepared functionalized nanomaterial.
Figure 3C:
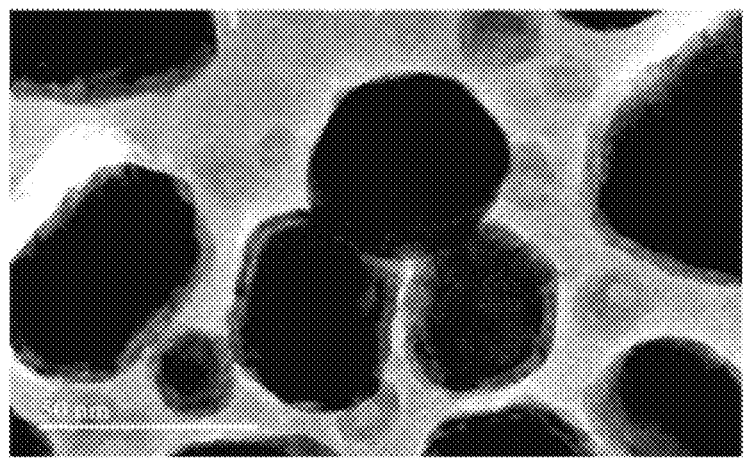
FIG. 3C is a TEM image of the prepared functionalized nanomaterial particulates demonstrating a 2 nm thickness of the bis(diarylphosphinomethyl) dopamine based ligand layer.
Figure 3D:
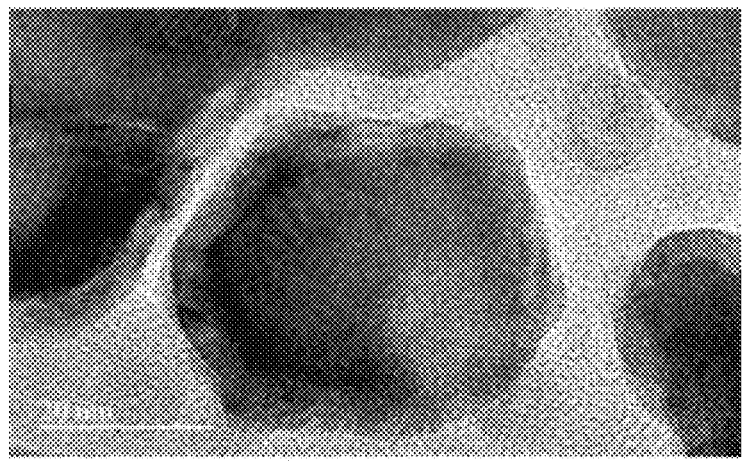
FIG. 3D is a TEM image of the magnified view of the prepared functionalized nanomaterial particulates demonstrating a 2 nm thickness of the bis(diarylphosphinomethyl) dopamine based ligand layer.
Figure 3E:
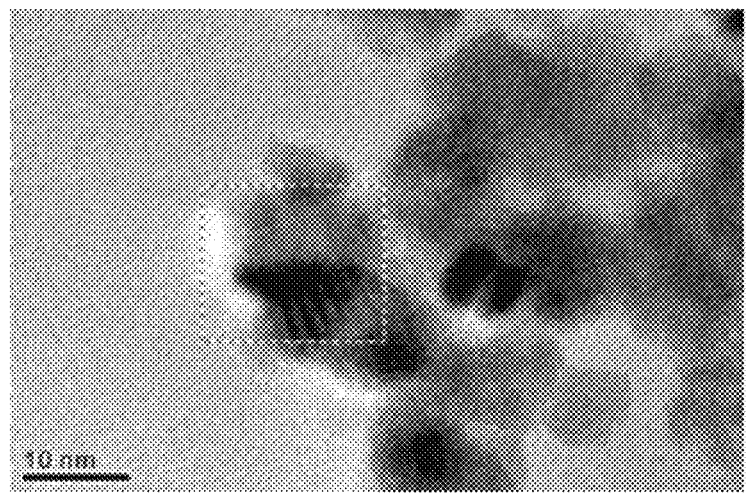
FIG. 3E is a high-resolution transmission electron microscopy (HRTEM) image of selected prepared functionalized nanomaterial particles.
Figure 3F:
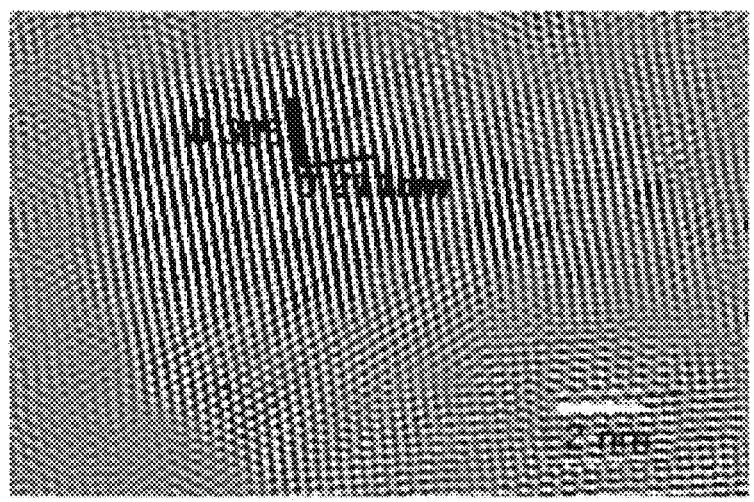
FIG. 3F is a HRTEM image of the magnified view of a selected prepared functionalized nanomaterial particle.
Figure 4:
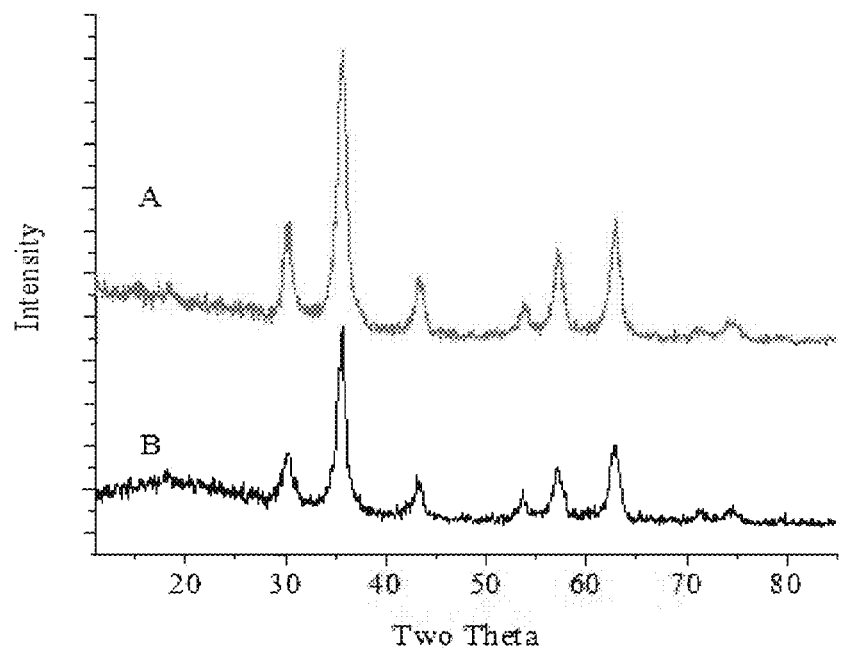
FIG. 4 is an X-ray diffraction (XRD) analysis wherein (A) is the XRD analysis of magnetite, $Fe_3O_4$, and (B) is the XRD analysis of the prepared functionalized nanomaterial.
Figure 7:
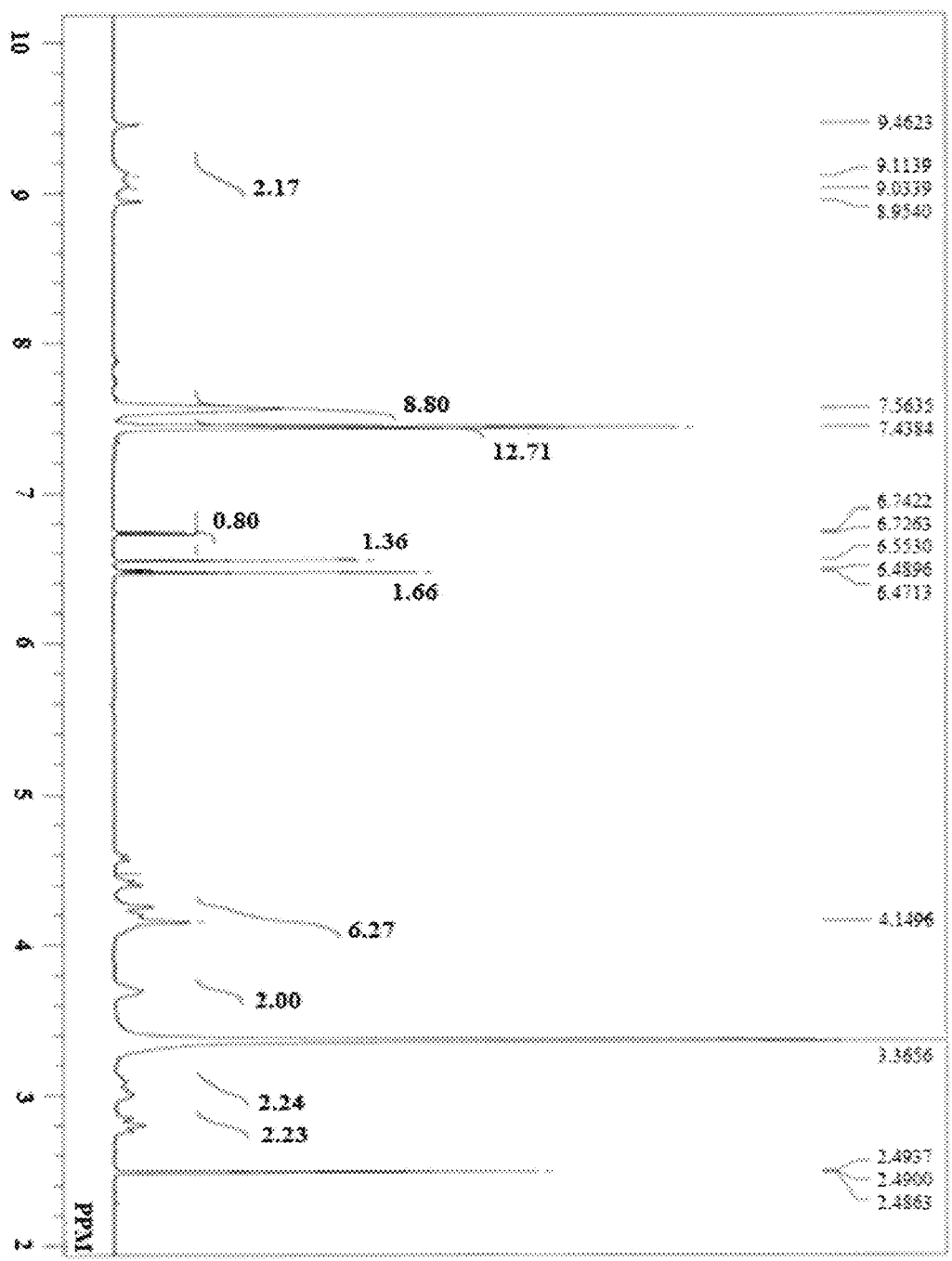
FIG. 7 is a $^1H$ nuclear magnetic resonance (NMR) spectra of the prepared bis(diarylphosphinomethyl) dopamine based ligand which is bis(diphenylphosphinomethyl) dopamine in $DMSO-d_6$.
Figure 8:
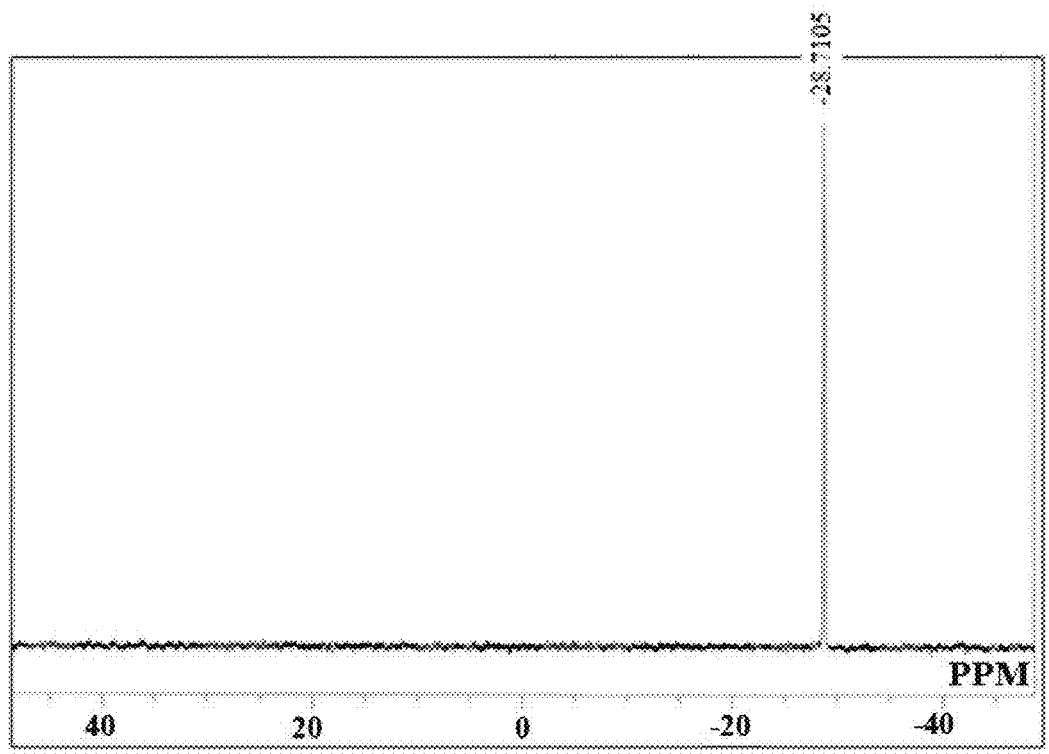
FIG. 8 is a $^{31}P$ NMR spectra of the prepared bis(diarylphosphinomethyl) dopamine based ligand which is bis(diphenylphosphinomethyl) dopamine in $DMSO-d_6$.

The phosphinylated ligand (bpd) was characterized by $^1$H and $^{31}$P nuclear magnetic resonance (NMR) spectroscopy in deuterated dimethyl sulfoxide (DMSO-d$_6$). In the $^1$H NMR, the shift of the $CH_2$—P proton at δ-4.14 ppm and its ethylene side chain was confirmed by the alkyl proton shift at 2.49 and 3.69 ppm (FIG. 7). $^{31}$P NMR exhibited shift at δ-28.72 ppm (FIG. 8) which is consistent with the literature data [P. Servin, R. Laurent, A. Romerosa, M. Peruzzini, J.-P. Majoral, and A.-M. Caminade, *Organometallics* 2008, 27, 2066; and O. Kuhl, S. Blaurock, J. Sieler and E. H. Hawkins, *Polyhedron* 2001, 20, 2171; and T. T. Co, S. C. Shim, C. S. Cho, T. J. Kim, S. O. Kang, W. S. Han, J. Ko, and C.-K. Kim, *Organometallics* 2005, 24, 4824—each incorporated herein by reference in its entirety]. The synthesized functionalized nanomaterials were imaged under transmission electron microscope (TEM) analysis (FIG. 3B) and found to be spherical and uniformly distributed. The typical core-shell structures of the functionalized nanomaterial particles were confirmed with spherical morphology and average diameter of 5-7 nm with the bis(methyldiphenylphosphino) dopamine ligand coating (FIG. 3C and FIG. 3D). The crystalline nature of the magnetite nanoparticles was ascertained from their XRD signature (FIG. 4) which was identical to that reported in the literature (JCPDS 2-1035), without the presence of any other oxide or hydroxide phases. The broad diffraction peaks confirmed the nanocrystalline nature of the material.

Figure 5:
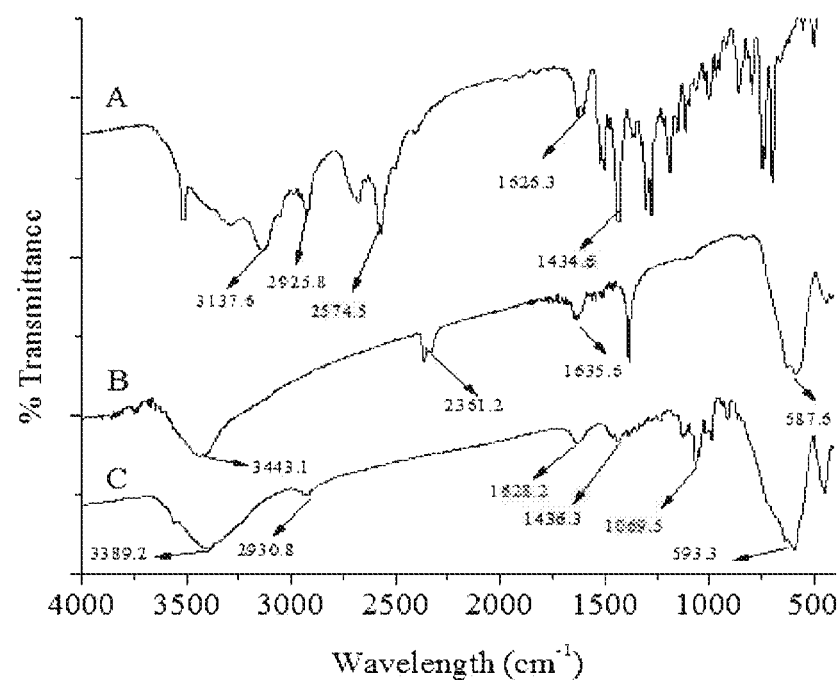
FIG. 5 is a Fourier transform infrared spectroscopy (FT-IR) analysis wherein (A) is the FT-IR analysis of bis (methyldiphenylphosphino) dopamine, (B) is the FT-IR analysis of magnetite, $Fe_3O_4$, and (C) is the FT-IR analysis of the prepared functionalized nanomaterial.
Figure 6:
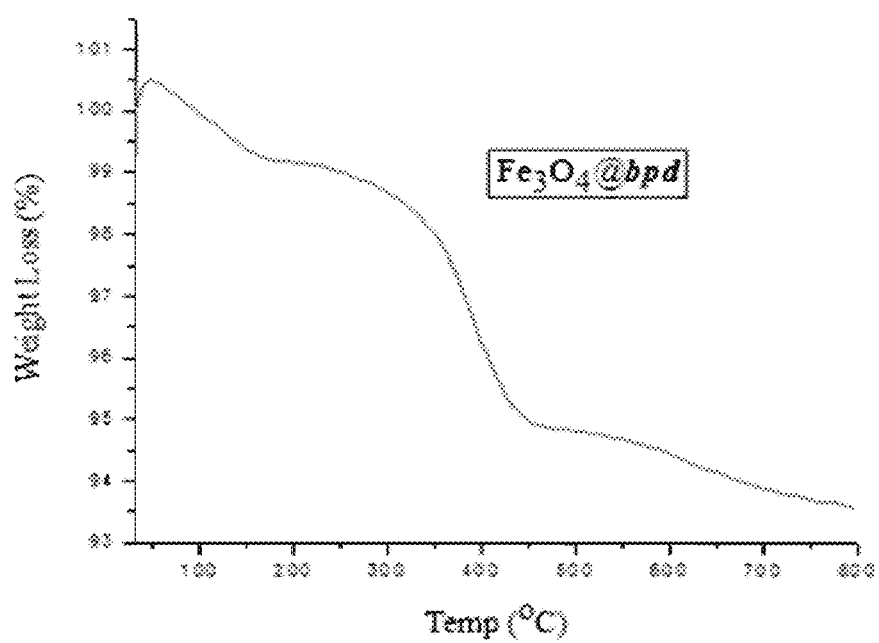
FIG. 6 is a thermal gravimetric analysis (TGA) of the prepared functionalized nanomaterial under argon atmosphere at a heating rate of 10° C./min.

The presence of the bpd ligand on the surface of magnetite nanoparticles was further characterized by the Fourier-transform infrared spectroscopy (FT-IR). The transmittance spectra of magnetic nanoparticles, bis(methyldiphenylphosphino) dopamine ligand, and the functionalized nanomaterial are shown in FIG. 5. All characteristic peaks of the dopamine compound were observed in the spectrum, in addition to the strong appearance of the Fe—O vibration shift at 593 cm$^{-1}$. The presence of 2930 cm$^{-1}$ (aromatic C—H stretching), 1628 cm$^{-1}$ and 1436 cm$^{-1}$ bands clearly demonstrates the anchoring of the phosphinylated dopamine on the surface of the particles. Thermal gravimetric analysis (TGA) studies were conducted to investigate the thermal stability as well as the strong attachment of the organic ligand on the magnetic nanoparticle surface. The data showed that the weight loss at temperatures ≤150° C. was because of the loss of water molecules [J. Hee Yang, B. Ramaraj and K. R. Yoon, *Journal of Alloys and Compounds* 2014, 583, 128.—incorporated herein by reference in its entirety]. The largest weight loss (~9%) occurred between 200 and ~450° C., which could be attributed to the elimination of ligands from the surface, in several steps. The amount of bis(methyldiphenylphosphino) dopamine ligand on the surface was measured by the phosphorous content. The ICP data yielded about 0.39 mmol of phosphine/g of the functionalized nanoagents. This is the highest amount of phosphine loading on the surface of magnetite reported at this time, and may be attributed to the small size of the ligand. It is well known that steric and bulky moieties occupy less area on the surface and a larger number of ligands are thus able to bind through the phenolic oxygen to the $Fe_3O_4$ core.

Figure 9:
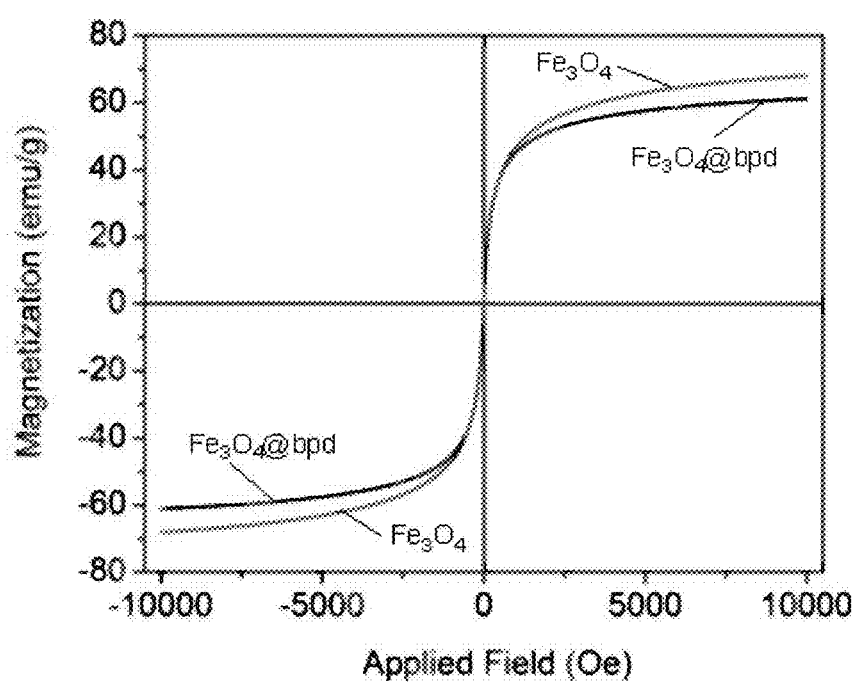
FIG. 9 is the magnetization-field (M-H) curves for the iron oxide nanoparticle core and the prepared functionalized nanomaterial recorded at room temperature.

Magnetization-field (M-H) curves recorded at room temperature are illustrated in FIG. 9. The superparamagnetic behavior for both samples of the magnetite nanoparticles and synthesized functionalized nanomaterials. In addition, the presence of a very small paramagnetic component (saturation cannot be reached) was observed and deduced using MicroMag software. It can be noted that the value of corecivity ($H_c$) is very small within the range of 2.98-3.97 Oe, while the remanence ($M_r$) decreases slightly from 0.802 emu/g for the magnetite nanoparticles to 0.658 emu/g for the functionalized nanomaterials. Similarly to the remanence, the saturation magnetization ($M_s$) reduces slightly by ~5 emu/g from the magnetite nanoparticles to the synthesized functionalized nanomaterials. The above changes are attributed to the attached bis(phosphinomethyl) dopamine ligands on the surface of the magnetite nanoparticles.

Example 7

Catalytic Hydroformylation Reaction and Analysis 30 mg of the functionalized nanomaterial with 1 mmol of appropriate substrate was placed in anhydrous THF in a 45 mL Teflon-lined autoclave. The [Rh(NBD)Cl]$_2$ was added to this solution under argon. The sealed autoclave was purged 3 times with syngas (1:1 CO and $H_2$), pressurized up to 200 psi and kept at 90° C. for 16 h. After cooling to room temperature, the catalyst was magnetically extracted, washed several times with dichloromethane and preserved for use in subsequent cycles.

The catalytic hydroformylation reaction was carried out on several olefins (Table 1 and Table 2) in the presence of the syngas at different temperatures in a sealed autoclave at a pressure of up to 200 psi. From Table 1, it is clear that the catalyst was very reactive and selective towards the branched aldehyde product in the low temperature regime. A reversal of selectivity was observed at high temperature for styrene, reaching up to ~1.5. For example, the catalytic reaction was run at room temperature (rt) and 50° C. for 24 hours using $RhCl_3$ as the metal precursor with styrene as the substrate in dry toluene, 35% and 100% conversion was observed with the selectivity of 0.20 and 0.47 with linear to branched aldehyde respectively. In this reaction a fair amount of hydrogenated product was also observed, which could be attributed to the lower solubility of $RhCl_3$ in toluene. This could mitigate the entrance of olefins into the hydroformylation catalytic cycles. When the reaction was carried out at 120° C., the linear aldehyde (a desired product) was the major product.

Significant changes were observed when dimeric Rh(NBD) in freshly distilled THF was used, the latter is considered a good solvent for hydroformylation over hydrogenation as it is reported to have led to formylation product at 90° C. [C. Duanmu, L. Wu, J. Gu, X. Xu, L. Feng and Xu Gu, *Catalysis Communications* 2014, 48, 45.—incorporated herein by reference in its entirety]. A series of substituted styrenes were studied to determine the reactivity of catalyst towards the electron withdrawing and electron donating groups in different positions of the aromatic ring but there was no significant difference observed [R. Abu-Reziq, H. Alper, D. Wang, and Michael L. Post, *J. Am. Chem. Soc.* 2013, 128, 5279.—incorporated herein by reference in its entirety] and it is confirmed by entry 5 and entry 7 in Table 1. In addition, the reactivity of 3-nitro styrene, entry 8 in Table 1, was found to be comparatively higher with regards to selectivity among the series at the same temperature.

TABLE 1

Hydroformylation[a] of olefins using MNP@bpd with the pressure of 200 psi using [Rh(NBD)Cl]$_2$ as metal precursor

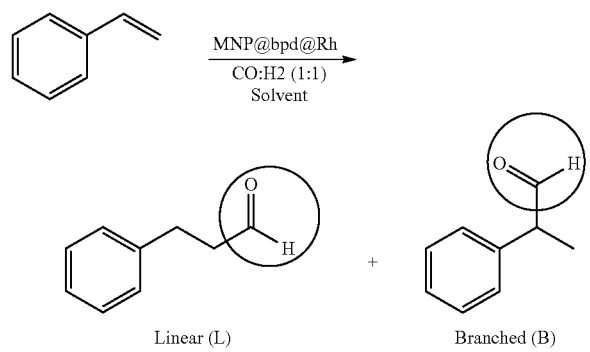

| Round # | Substrate(s) | Time (h) | Solvent | Temp (° C.) | Conversion[b] (%) | L | B | Ratio[c] (L:B) |
|---|---|---|---|---|---|---|---|---|
| 1[d] | Styrene | 24 | Toluene | rt | 35 | 6 | 29 | 0.20 |
| 2[d] | Styrene | 24 | Toluene | 50 | 100 | 32 | 68 | 0.47 |
| 3[d] | Styrene | 20 | THF | 120 | 100 | 60 | 40 | 1.50 |

TABLE 1-continued

Hydroformylation[a] of olefins using MNP@bpd with the pressure of 200 psi using [Rh(NBD)Cl]$_2$ as metal precursor

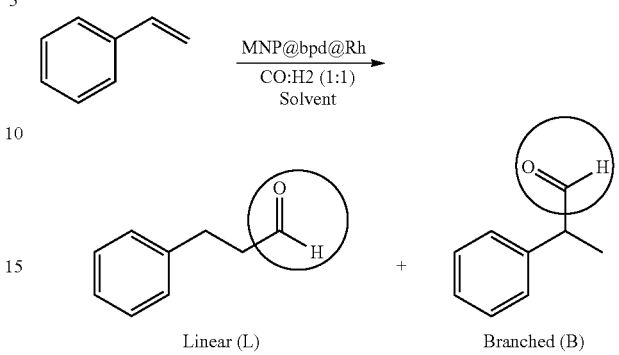

| Round # | Substrate(s) | Time (h) | Solvent | Temp (° C.) | Conversion[b] (%) | L | B | Ratio[c] (L:B) |
|---|---|---|---|---|---|---|---|---|
| 4 | Styrene | 22 | THF | 90 | 100 | 48 | 52 | 0.92 |
| 5 | 4-Methylsyrene | 19 | THF | 90 | 100 | 50 | 42 | 1.19 |
| 6 | 4-Vinylanisole | 18 | THF | 90 | 100 | 46 | 54 | 0.85 |
| 7 | 4-Chlorostyrene | 18 | THF | 90 | 100 | 56 | 44 | 1.27 |
| 8 | 3-Nitrostyrene | 16 | THF | 90 | 100 | 57 | 43 | 1.32 |

[a]1 mmol of styrene in 10 mL anhydrous solvent under 200 psi pressure in presence of syngas (CO:H$_2$, 1:1) using 30 mg of catalyst
[b]determined by GC
[c]determined by GC-MS
[d]with RhCl$_3$ The functionalized nanomaterial or nanocatalysts were recycled (Table 2) after washing several times to remove all materials present after the first round of catalysis and recovered through the use of a magnet. The nanocatalysts were recycled at the same temperature, pressure and duration and maintained significant activity even through a fourth round of reactions. For entry 1 in Table 2, it was demonstrated that with the use of the 30 mg of catalyst, the functionalized nanomaterial, and the corresponding amount of [Rh(NBD)Cl]$_2$ the selectivity ratio was 0.92 and this trend persisted through the second round of reactions. However, in the third and fourth round of reactions the selectivity was reversed due to unknown reasons.

TABLE 2

Recycling of Fe$_3$O$_4$ @ bpd @ Rh of styrene as substrate for hydroformylation[a]

| Round # | Substrate(s) | Conversion[b] (%) | Linear | Branched | Ratio[c] (L:B) |
|---|---|---|---|---|---|
| 1 | Styrene | 100 | 48 | 52 | 0.92 |
| 2 | Styrene | 97 | 43 | 54 | 0.79 |
| 3 | Styrene | 84 | 46 | 38 | 1.21 |
| 4 | Styrene | 69 | 38 | 31 | 1.23 |

[a]1 mmol of styrene in 10 mL anhydrous freshly distilled THF at 90° C. under 200 psi pressure in presence of syngas (CO:H$_2$, 1:1) using 30 mg of catalyst for 22 h
[b]determined by GC
[c]determined by GC-MS Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for hydroformylating an olefin to form an aldehyde, comprising;
   mixing a catalyst composition with the olefin,
   wherein the catalyst composition comprises a functionalized nanomaterial, comprising;
   an iron oxide nanoparticle core, and
   a bis(diarylphosphinomethyl) dopamine ligand of formula (I):

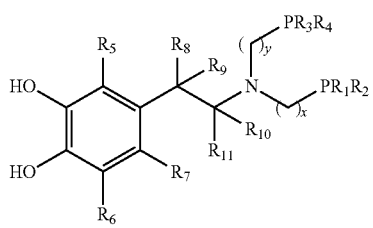

wherein the aryl hydroxyl groups are deprotonated when anchored to the surface of the iron oxide nanoparticle core,
   $R_1$, $R_2$, $R_3$ and $R_4$ are aryl groups,
   x and y are each independently from 1 to 10, and
   $R_5$-$R_{10}$ are each independently a halogen, an aryl group, a $C_1$-$C_{10}$ alkyl group, an alkoxyl group, and a nitro group,
   wherein the bis(diarylphosphinomethyl) dopamine ligand is anchored to a surface of the iron oxide nanoparticle core by phenolic hydroxide groups to form a bis(diarylphosphinomethyl) dopamine ligand layer, and
   wherein the bisphosphine groups of the bis(diarylphosphinomethyl) dopamine ligand chelate at least one catalytic metal selected from the group consisting of nickel, platinum, palladium, rhodium, iron, silver, ruthenium and iridium, and
   hydroformylating the olefin carbon monoxide in the presence of the catalyst composition to form the aldehyde.

2. The method of claim 1, further comprising recovering and reusing the functionalized nanomaterial in at least two reaction iterations.

3. The method of claim 1, wherein the metal is rhodium.

4. The method of claim 1, wherein the olefin is a styrene.

5. The method of claim 1, wherein greater than 90% of the olefin is converted to the aldehyde by the hydroformylating.

6. The method of claim 1, wherein the mixing involves no more than 50 mg of the functionalized nanomaterial per 1.0 mmol of olefin.

7. The method of claim 1, wherein the aldehyde has a linear aldehyde form and a branched aldehyde form and the ratio of the linear aldehyde form to the branched aldehyde form is greater than or equal to 1.

* * * * *